US010993960B1

(12) United States Patent
Kataoka et al.

(10) Patent No.: US 10,993,960 B1
(45) Date of Patent: May 4, 2021

(54) PHARMACEUTICAL COMPOSITION

(71) Applicant: KAWASAKI INSTITUTE OF INDUSTRIAL PROMOTION, Kawasaki-shi (JP)

(72) Inventors: Kazunori Kataoka, Tokyo (JP); Takehiko Ishii, Tokyo (JP); Mitsuru Naito, Tokyo (JP); Naoto Yoshinaga, Tokyo (JP); Taisuke Endo, Tokyo (JP)

(73) Assignee: KAWASAKI INSTITUTE OF INDUSTRIAL PROMOTION, Kawasaki (JP)

( * ) Notice: Subject to any disclaimer, the term of this patent is extended or adjusted under 35 U.S.C. 154(b) by 0 days.

(21) Appl. No.: 15/309,310

(22) PCT Filed: May 8, 2015

(86) PCT No.: PCT/JP2015/063363
§ 371 (c)(1),
(2) Date: Jun. 5, 2017

(87) PCT Pub. No.: WO2015/170757
PCT Pub. Date: Nov. 12, 2015

(30) Foreign Application Priority Data

May 8, 2014 (JP) .............................. JP2014-097219

(51) Int. Cl.
*A61K 31/711* (2006.01)
*A61K 9/107* (2006.01)
*A61K 47/34* (2017.01)
*A61K 31/7105* (2006.01)
*A61K 48/00* (2006.01)

(52) U.S. Cl.
CPC ............ *A61K 31/711* (2013.01); *A61K 9/107* (2013.01); *A61K 31/7105* (2013.01); *A61K 47/34* (2013.01); *A61K 48/00* (2013.01)

(58) Field of Classification Search
CPC .. C07F 5/025; G01N 33/54353; G01N 33/66; G01N 27/4145; G01N 33/582; G01N 2610/00; G01N 33/533; G01N 33/542; G01N 33/531; G01N 21/553; G01N 33/54373; G01N 33/553; G01N 2400/00; G01N 13/04; G01N 2030/484; G01N 2030/8831; G01N 2030/8836; G01N 21/453; G01N 21/4788; G01N 2333/62; G01N 24/08; G01N 27/3275; G01N 27/4166; G01N 30/90; G01N 33/50; G01N 33/5308; G01N 33/54326; G01N 33/54346; G01N 33/551; G01N 33/552; G01N 33/74; G01N 5/02; G01N 7/00; G01N 1/405; G01N 2021/6484; G01N 2021/772; G01N 2021/7723; G01N 2021/7786; G01N 21/645; G01N 21/6486; G01N 21/7703; G01N 21/8507; G01N 2201/08; G01N 2560/00; G01N 27/327; G01N 27/414; G01N 27/4161; G01N 33/558; G01N 33/6851; C07C 229/38; C07C 233/49; C07C 237/22; C07C 255/13; C07C 259/10; C07C 271/22; C07C 281/02; C07C 233/51; C07C 237/12; Y10T 436/144444; Y10T 436/143333; Y10T 436/142222; Y10T 436/14; Y10T 436/147777; Y10T 436/16; Y10T 436/171538; Y10T 436/175383; Y10T 436/19; Y10T 436/201666; Y10T 436/204998; Y10T 436/207497; Y10T 436/24
USPC ......................................... 424/450, 486, 489
See application file for complete search history.

(56) References Cited

U.S. PATENT DOCUMENTS

| 5,780,454 A | 7/1998 | Adams et al. |
| 9,114,177 B2 * | 8/2015 | Kataoka ................. C08G 81/00 |
| 2008/0248097 A1 | 10/2008 | Kwon et al. |

(Continued)

FOREIGN PATENT DOCUMENTS

| JP | H05301880 A | 11/1993 |
| JP | H083172 A | 1/1996 |

(Continued)

OTHER PUBLICATIONS

Akira Matsumoto et al: "Glucose-Responsive Polymer Bearing a Novel Phenylborate Derivative as a Glucose-Sensing Moiety Operating at Physiological pH Conditions", Biomacromolecules, vol. 4, No. 5, Aug. 19, 2003 (Aug. 19, 2003), pp. 1410-1416, XP055105744, ISSN: 1525-7797.

(Continued)

*Primary Examiner* — Janet L Epps-Smith
(74) *Attorney, Agent, or Firm* — J-Tek Law PLLC; Jeffrey D. Tekanic; Scott T. Wakeman

(57) ABSTRACT

A pharmaceutical composition includes polymer units α and β, each having a hydrophilic polymer chain bound to a cationic polymer chain, and a drug. The polymer units α and β are radially arranged such that the cationic polymer chains are directed inward and the hydrophilic polymer chains are directed outward, thereby forming a micelle with the drug encapsulated in the micelle. The cationic polymer chain of the polymer unit α has a phenylboronic acid group in a side chain, and the cationic polymer chain of the polymer unit β has a phenylboronic acid binding site in a side chain. The phenylboronic acid group and the phenylboronic acid binding site form a cross-linked structure that can dissociate in an acidic environment and/or in the presence of a substance capable of competitive binding.

15 Claims, 7 Drawing Sheets

Specification includes a Sequence Listing.

(56) References Cited

U.S. PATENT DOCUMENTS

| | | |
|---|---|---|
| 2010/0040556 A1 | 2/2010 | Davis et al. |
| 2010/0167416 A1* | 7/2010 | Kabilan .............. G01N 21/4788 436/501 |
| 2010/0221320 A1 | 9/2010 | Kato et al. |
| 2010/0247669 A1 | 9/2010 | Eliasof et al. |
| 2010/0285094 A1* | 11/2010 | Gupta ..................... A61L 15/60 424/429 |
| 2010/0298495 A1 | 11/2010 | Bobe et al. |
| 2011/0142787 A1 | 6/2011 | Nagasaki et al. |
| 2012/0053295 A1 | 3/2012 | Kataoka et al. |
| 2012/0093881 A1 | 4/2012 | Kato et al. |
| 2012/0149649 A1 | 6/2012 | Kato et al. |
| 2012/0283403 A1 | 11/2012 | Matsumoto et al. |
| 2014/0017192 A1 | 1/2014 | Saito et al. |
| 2014/0017328 A1 | 1/2014 | Kataoka et al. |
| 2015/0051347 A1 | 2/2015 | Kataoka et al. |
| 2016/0114058 A1 | 4/2016 | Kato et al. |

FOREIGN PATENT DOCUMENTS

| | | | |
|---|---|---|---|
| JP | 2002179683 A | 6/2002 | |
| JP | 2011140537 A | 7/2011 | |
| JP | 2011173960 A | 9/2011 | |
| JP | 2012500208 A | 1/2012 | |
| JP | 2016517393 A | 6/2016 | |
| WO | 9613266 A | 5/1996 | |
| WO | 2009133647 A | 11/2009 | |
| WO | 2010019718 A | 2/2010 | |
| WO | 2012133884 A | 10/2012 | |
| WO | WO-2013073697 A1 * | 5/2013 | ............. C08G 81/00 |
| WO | 2014133549 A1 | 9/2014 | |

OTHER PUBLICATIONS

Cheng et al. "Phenylboronic acid-containing block copolymers: synthesis, self-assembly,and application for intracellular delivery of proteins", New Journal of Chemistry, 2012, 36(6), pp. 1413-1421.

Deshayes et al., "Phenylboronic Acid-Installed Polymeric Micelles for Targeting Sialylated Epitopes in Solid Tumors," Journal of the American Chemical Society, 2013, 135(41), pp. 15501-15507.

English translation of International Search Report dated Jul. 14, 2015 in parent application No. PCT/JP2015/063363.

F. Nakanowatari et al., "Micelle formation from PEG-p(Lys) block copolymer with phenyl boronic acid moieties", Polymer Preprints, Japan, May 1999, vol. 48, No. 3, p. 572, including English translation thereof.

K. Kataoka, "Cellular specific material and new drug delivery system" Polyfile, Apr. 1993, pp. 27-31, including English translation thereof.

L. Zhao et al., "Glucose-sensitive polypeptide micelles for self-regulated insulin release at physiological pH", J. Mater. Chem., 2012, vol. 22, pp. 12319-12328.

M. Naito et al., "Design and physicochemical evaluation of novel polymeric micelle forming reversible covalent bond with ribose for siRNA delivery carrier", Polymer Preprints, Japan, May 2012, vol. 61, No. 1, p. 1642, including English abstract at bottom of page.

Miyata et al: "PEG-based block catiomers possessing DNA anchoring and endosomal escaping functions to form polyplex micelles with improved stability and high transfection efficacy"; Journal of Controlled Release, Elsevier, Amsterdam, NL, vol. 122, No. 3; Sep. 18, 2007 (Sep. 18, 2007), pp. 252-260, XP022336556, ISSN: 0168-3659

Naoto Yoshinaga et al., "Phenylboronic Acid Kobunshi Micelle Core no Kakyozai to shite Mochiiru Saibonai Kankyo Oto-gata Kakusan Delivery System no Soshutsu", Polymer Preprints, Japan (CD-ROM), May 9, 2014, 63 (1), pp. 3539-3540, including English abstract at bottom of page and English translation at the end of the document.

Singhal RP et al: "New ligands for boronate affinity chromatography"; Journal of Chromatography, Elsevier Science Publishers B.V, NL, vol. 543, Jan. 1, 1991 (Jan. 1, 1991), pp. 17-38, XP026514921; ISSN: 0021-9673.

English translation of Written Opinion of the International Searching Authority dated Jul. 14, 2015 in parent application No. PCT/JP2015/063363.

Office Action from the Japanese Patent Office dated Jan. 22, 2019 in counterpart Japanese application No. 2016-517950, and machine translation thereof.

English translation of Decision to Grant a Patent dispatched by the JPO dated Jul. 9, 2019 in counterpart JP application No. 2016-517950.

Extended European Search Report dated Oct. 25, 2017 in counterpart EP application No. 15789186, including Search Opinion, Supplementary European Search Report and allowed claims 1-5.

Communication of Intention to Grant dated Jan. 8, 2020 in counterpart EP application No. 15789186.

* cited by examiner (1) naked DNA
(2) INTRODUCTION NUMBER OF POLYOL 7
(3) INTRODUCTION NUMBER OF POLYOL 11
(4) INTRODUCTION NUMBER OF POLYOL 20
(5) INTRODUCTION NUMBER OF POLYOL 40

(1) naked pDNA
(2) ATP 0.3mM
(3) ATP 0.5mM
(4) ATP 1.0mM
(5) ATP 3.0mM
(6) ATP 5.0mM

SEQUENCE LISTING

```
<160> NUMBER OF SEQ ID NOS: 4

<210> SEQ ID NO 1
<211> LENGTH: 1653
<212> TYPE: DNA
<213> ORGANISM: Photinus pyralis
<220> FEATURE:
<221> NAME/KEY: CDS
<222> LOCATION: (1)..(1653)

<400> SEQUENCE: 1 atg gaa gac gcc aaa aac ata aag aaa ggc ccg gcg cca ttc tat ccg      48
Met Glu Asp Ala Lys Asn Ile Lys Lys Gly Pro Ala Pro Phe Tyr Pro
1               5                   10                  15 ctg gaa gat gga acc gct gga gag caa ctg cat aag gct atg aag aga      96
Leu Glu Asp Gly Thr Ala Gly Glu Gln Leu His Lys Ala Met Lys Arg
```

-continued

```
              20                  25                  30
tac gcc ctg gtt cct gga aca att gct ttt aca gat gca cat atc gag      144
Tyr Ala Leu Val Pro Gly Thr Ile Ala Phe Thr Asp Ala His Ile Glu
         35                  40                  45 gtg gac atc act tac gct gag tac ttc gaa atg tcc gtt cgg ttg gca      192
Val Asp Ile Thr Tyr Ala Glu Tyr Phe Glu Met Ser Val Arg Leu Ala
 50                  55                  60 gaa gct atg aaa cga tat ggg ctg aat aca aat cac aga atc gtc gta      240
Glu Ala Met Lys Arg Tyr Gly Leu Asn Thr Asn His Arg Ile Val Val
 65                  70                  75                  80 tgc agt gaa aac tct ctt caa ttc ttt atg ccg gtt ttg ggc gcg tta      288
Cys Ser Glu Asn Ser Leu Gln Phe Phe Met Pro Val Leu Gly Ala Leu
                 85                  90                  95 ttt atc gga gtt gca gtt gcg ccc gcg aac gac att tat aat gaa cgt      336
Phe Ile Gly Val Ala Val Ala Pro Ala Asn Asp Ile Tyr Asn Glu Arg
             100                 105                 110 gaa ttg ctc aac agt atg ggc att tcg cag cct acc gtg gtg ttc gtt      384
Glu Leu Leu Asn Ser Met Gly Ile Ser Gln Pro Thr Val Val Phe Val
         115                 120                 125 tcc aaa aag ggg ttg caa aaa att ttg aac gtg caa aaa aag ctc cca      432
Ser Lys Lys Gly Leu Gln Lys Ile Leu Asn Val Gln Lys Lys Leu Pro
130                 135                 140 atc atc caa aaa att att atc atg gat tct aaa acg gat tac cag gga      480
Ile Ile Gln Lys Ile Ile Ile Met Asp Ser Lys Thr Asp Tyr Gln Gly
145                 150                 155                 160 ttt cag tcg atg tac acg ttc gtc aca tct cat cta cct ccc ggt ttt      528
Phe Gln Ser Met Tyr Thr Phe Val Thr Ser His Leu Pro Pro Gly Phe
                 165                 170                 175 aat gaa tac gat ttt gtg cca gag tcc ttc gat agg gac aag aca att      576
Asn Glu Tyr Asp Phe Val Pro Glu Ser Phe Asp Arg Asp Lys Thr Ile
             180                 185                 190 gca ctg atc atg aac tcc tct gga tct act ggt ctg cct aaa ggt gtc      624
Ala Leu Ile Met Asn Ser Ser Gly Ser Thr Gly Leu Pro Lys Gly Val
         195                 200                 205 gct ctg cct cat aga act gcc tgc gtg aga ttc tcg cat gcc aga gat      672
Ala Leu Pro His Arg Thr Ala Cys Val Arg Phe Ser His Ala Arg Asp
210                 215                 220 cct att ttt ggc aat caa atc att ccg gat act gcg att tta agt gtt      720
Pro Ile Phe Gly Asn Gln Ile Ile Pro Asp Thr Ala Ile Leu Ser Val
225                 230                 235                 240 gtt cca ttc cat cac ggt ttt gga atg ttt act aca ctc gga tat ttg      768
Val Pro Phe His His Gly Phe Gly Met Phe Thr Thr Leu Gly Tyr Leu
                 245                 250                 255 ata tgt gga ttt cga gtc gtc tta atg tat aga ttt gaa gaa gag ctg      816
Ile Cys Gly Phe Arg Val Val Leu Met Tyr Arg Phe Glu Glu Glu Leu
             260                 265                 270 ttt ctg agg agc ctt cag gat tac aag att caa agt gcg ctg ctg gtg      864
Phe Leu Arg Ser Leu Gln Asp Tyr Lys Ile Gln Ser Ala Leu Leu Val
         275                 280                 285 cca acc cta ttc tcc ttc ttc gcc aaa agc act ctg att gac aaa tac      912
Pro Thr Leu Phe Ser Phe Phe Ala Lys Ser Thr Leu Ile Asp Lys Tyr
290                 295                 300 gat tta tct aat tta cac gaa att gct tct ggt ggc gct ccc ctc tct      960
Asp Leu Ser Asn Leu His Glu Ile Ala Ser Gly Gly Ala Pro Leu Ser
305                 310                 315                 320 aag gaa gtc ggg gaa gcg gtt gcc aag agg ttc cat ctg cca ggt atc     1008
Lys Glu Val Gly Glu Ala Val Ala Lys Arg Phe His Leu Pro Gly Ile
                 325                 330                 335 agg caa gga tat ggg ctc act gag act aca tca gct att ctg att aca     1056
```

-continued

```

Arg Gln Gly Tyr Gly Leu Thr Glu Thr Thr Ser Ala Ile Leu Ile Thr
                340                 345                 350 ccc gag ggg gat gat aaa ccg ggc gcg gtc ggt aaa gtt gtt cca ttt      1104
Pro Glu Gly Asp Asp Lys Pro Gly Ala Val Gly Lys Val Val Pro Phe
            355                 360                 365 ttt gaa gcg aag gtt gtg gat ctg gat acc ggg aaa acg ctg ggc gtt      1152
Phe Glu Ala Lys Val Val Asp Leu Asp Thr Gly Lys Thr Leu Gly Val
370                 375                 380 aat caa aga ggc gaa ctg tgt gtg aga ggt cct atg att atg tcc ggt      1200
Asn Gln Arg Gly Glu Leu Cys Val Arg Gly Pro Met Ile Met Ser Gly
385                 390                 395                 400 tat gta aac aat ccg gaa gcg acc aac gcc ttg att gac aag gat gga      1248
Tyr Val Asn Asn Pro Glu Ala Thr Asn Ala Leu Ile Asp Lys Asp Gly
                405                 410                 415 tgg cta cat tct gga gac ata gct tac tgg gac gaa gac gaa cac ttc      1296
Trp Leu His Ser Gly Asp Ile Ala Tyr Trp Asp Glu Asp Glu His Phe
            420                 425                 430 ttc atc gtt gac cgc ctg aag tct ctg att aag tac aaa ggc tat cag      1344
Phe Ile Val Asp Arg Leu Lys Ser Leu Ile Lys Tyr Lys Gly Tyr Gln
435                 440                 445 gtg gct ccc gct gaa ttg gaa tcc atc ttg ctc caa cac ccc aac atc      1392
Val Ala Pro Ala Glu Leu Glu Ser Ile Leu Leu Gln His Pro Asn Ile
450                 455                 460 ttc gac gca ggt gtc gca ggt ctt ccc gac gat gac gcc ggt gaa ctt      1440
Phe Asp Ala Gly Val Ala Gly Leu Pro Asp Asp Asp Ala Gly Glu Leu
465                 470                 475                 480 ccc gcc gcc gtt gtt gtt ttg gag cac gga aag acg atg acg gaa aaa      1488
Pro Ala Ala Val Val Val Leu Glu His Gly Lys Thr Met Thr Glu Lys
                485                 490                 495 gag atc gtg gat tac gtc gcc agt caa gta aca acc gcg aaa aag ttg      1536
Glu Ile Val Asp Tyr Val Ala Ser Gln Val Thr Thr Ala Lys Lys Leu
            500                 505                 510 cgc gga gga gtt gtg ttt gtg gac gaa gta ccg aaa ggt ctt acc gga      1584
Arg Gly Gly Val Val Phe Val Asp Glu Val Pro Lys Gly Leu Thr Gly
515                 520                 525 aaa ctc gac gca aga aaa atc aga gag atc ctc ata aag gcc aag aag      1632
Lys Leu Asp Ala Arg Lys Ile Arg Glu Ile Leu Ile Lys Ala Lys Lys
530                 535                 540 ggc gga aag atc gcc gtg taa                                          1653
Gly Gly Lys Ile Ala Val
545                 550
```

<210> SEQ ID NO 2
<211> LENGTH: 550
<212> TYPE: PRT
<213> ORGANISM: Photinus pyralis

<400> SEQUENCE: 2

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
```

-continued

```
                    85                  90                  95
Phe Ile Gly Val Ala Val Ala Pro Ala Asn Asp Ile Tyr Asn Glu Arg
                100                 105                 110

Glu Leu Leu Asn Ser Met Gly Ile Ser Gln Pro Thr Val Val Phe Val
            115                 120                 125

Ser Lys Lys Gly Leu Gln Lys Ile Leu Asn Val Gln Lys Lys Leu Pro
        130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510
```

```
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ile Ala Val
545                 550

<210> SEQ ID NO 3
<211> LENGTH: 1653
<212> TYPE: DNA
<213> ORGANISM: Photinus pyralis
<220> FEATURE:
<221> NAME/KEY: CDS
<222> LOCATION: (1)..(1653)

<400> SEQUENCE: 3
```

| | | | | | | | | | | | | | | | | |
|---|---|---|---|---|---|---|---|---|---|---|---|---|---|---|---|---|
| atg | gaa | gat | gcc | aaa | aac | att | aag | aag | ggc | cca | gcg | cca | ttc | tac | cca | 48 |
| Met | Glu | Asp | Ala | Lys | Asn | Ile | Lys | Lys | Gly | Pro | Ala | Pro | Phe | Tyr | Pro | |
| 1 | | | | 5 | | | | | 10 | | | | | 15 | | |
| ctc | gaa | gac | ggg | acc | gcc | ggc | gag | cag | ctg | cac | aaa | gcc | atg | aag | cgc | 96 |
| Leu | Glu | Asp | Gly | Thr | Ala | Gly | Glu | Gln | Leu | His | Lys | Ala | Met | Lys | Arg | |
| | | | 20 | | | | | 25 | | | | | 30 | | | |
| tac | gcc | ctg | gtg | ccc | ggc | acc | atc | gcc | ttt | acc | gac | gca | cat | atc | gag | 144 |
| Tyr | Ala | Leu | Val | Pro | Gly | Thr | Ile | Ala | Phe | Thr | Asp | Ala | His | Ile | Glu | |
| | | 35 | | | | | 40 | | | | | 45 | | | | |
| gtg | gac | att | acc | tac | gcc | gag | tac | ttc | gag | atg | agc | gtt | cgg | ctg | gca | 192 |
| Val | Asp | Ile | Thr | Tyr | Ala | Glu | Tyr | Phe | Glu | Met | Ser | Val | Arg | Leu | Ala | |
| | 50 | | | | | 55 | | | | | 60 | | | | | |
| gaa | gct | atg | aag | cgc | tat | ggg | ctg | aat | aca | aac | cat | cgg | atc | gtg | gtg | 240 |
| Glu | Ala | Met | Lys | Arg | Tyr | Gly | Leu | Asn | Thr | Asn | His | Arg | Ile | Val | Val | |
| 65 | | | | | 70 | | | | | 75 | | | | | 80 | |
| tgc | agc | gag | aat | agc | ttg | cag | ttc | ttc | atg | ccc | gtg | ttg | ggt | gcc | ctg | 288 |
| Cys | Ser | Glu | Asn | Ser | Leu | Gln | Phe | Phe | Met | Pro | Val | Leu | Gly | Ala | Leu | |
| | | | | 85 | | | | | 90 | | | | | 95 | | |
| ttc | atc | ggt | gtg | gct | gtg | gcc | cca | gct | aac | gac | atc | tac | aac | gag | cgc | 336 |
| Phe | Ile | Gly | Val | Ala | Val | Ala | Pro | Ala | Asn | Asp | Ile | Tyr | Asn | Glu | Arg | |
| | | | 100 | | | | | 105 | | | | | 110 | | | |
| gag | ctg | ctg | aac | agc | atg | ggc | atc | agc | cag | ccc | acc | gtc | gta | ttc | gtg | 384 |
| Glu | Leu | Leu | Asn | Ser | Met | Gly | Ile | Ser | Gln | Pro | Thr | Val | Val | Phe | Val | |
| | | 115 | | | | | 120 | | | | | 125 | | | | |
| agc | aag | aaa | ggg | ctg | caa | aag | atc | ctc | aac | gtg | caa | aag | aag | cta | ccg | 432 |
| Ser | Lys | Lys | Gly | Leu | Gln | Lys | Ile | Leu | Asn | Val | Gln | Lys | Lys | Leu | Pro | |
| | 130 | | | | | 135 | | | | | 140 | | | | | |
| atc | ata | caa | aag | atc | atc | atc | atg | gat | agc | aag | acc | gac | tac | cag | ggc | 480 |
| Ile | Ile | Gln | Lys | Ile | Ile | Ile | Met | Asp | Ser | Lys | Thr | Asp | Tyr | Gln | Gly | |
| 145 | | | | | 150 | | | | | 155 | | | | | 160 | |
| ttc | caa | agc | atg | tac | acc | ttc | gtg | act | tcc | cat | ttg | cca | ccc | ggc | ttc | 528 |
| Phe | Gln | Ser | Met | Tyr | Thr | Phe | Val | Thr | Ser | His | Leu | Pro | Pro | Gly | Phe | |
| | | | | 165 | | | | | 170 | | | | | 175 | | |
| aac | gag | tac | gac | ttc | gtg | ccc | gag | agc | ttc | gac | cgg | gac | aaa | acc | atc | 576 |
| Asn | Glu | Tyr | Asp | Phe | Val | Pro | Glu | Ser | Phe | Asp | Arg | Asp | Lys | Thr | Ile | |
| | | | 180 | | | | | 185 | | | | | 190 | | | |
| gcc | ctg | atc | atg | aac | agt | agt | ggc | agt | acc | gga | ttg | ccc | aag | ggc | gta | 624 |
| Ala | Leu | Ile | Met | Asn | Ser | Ser | Gly | Ser | Thr | Gly | Leu | Pro | Lys | Gly | Val | |
| | | 195 | | | | | 200 | | | | | 205 | | | | |
| gcc | cta | ccg | cac | cgc | acc | gct | tgt | gtc | cga | ttc | agt | cat | gcc | cgc | gac | 672 |
| Ala | Leu | Pro | His | Arg | Thr | Ala | Cys | Val | Arg | Phe | Ser | His | Ala | Arg | Asp | |
| | 210 | | | | | 215 | | | | | 220 | | | | | |
| ccc | atc | ttc | ggc | aac | cag | atc | atc | ccc | gac | acc | gct | atc | ctc | agc | gtg | 720 |
| Pro | Ile | Phe | Gly | Asn | Gln | Ile | Ile | Pro | Asp | Thr | Ala | Ile | Leu | Ser | Val | |

-continued

```
                 225                 230                 235                 240
gtg cca ttt cac cac ggc ttc ggc atg ttc acc acg ctg ggc tac ttg        768
Val Pro Phe His His Gly Phe Gly Met Phe Thr Thr Leu Gly Tyr Leu
                    245                 250                 255 atc tgc ggc ttt cgg gtc gtg ctc atg tac cgc ttc gag gag gag cta        816
Ile Cys Gly Phe Arg Val Val Leu Met Tyr Arg Phe Glu Glu Glu Leu
                260                 265                 270 ttc ttg cgc agc ttg caa gac tat aag att caa tct gcc ctg ctg gtg        864
Phe Leu Arg Ser Leu Gln Asp Tyr Lys Ile Gln Ser Ala Leu Leu Val
            275                 280                 285 ccc aca cta ttt agc ttc ttc gct aag agc act ctc atc gac aag tac        912
Pro Thr Leu Phe Ser Phe Phe Ala Lys Ser Thr Leu Ile Asp Lys Tyr
        290                 295                 300 gac cta agc aac ttg cac gag atc gcc agc ggc ggg gcg ccg ctc agc        960
Asp Leu Ser Asn Leu His Glu Ile Ala Ser Gly Gly Ala Pro Leu Ser
305                 310                 315                 320 aag gag gta ggt gag gcc gtg gcc aaa cgc ttc cac cta cca ggc atc       1008
Lys Glu Val Gly Glu Ala Val Ala Lys Arg Phe His Leu Pro Gly Ile
                    325                 330                 335 cgc cag ggc tac ggc ctg aca gaa aca acc agc gcc att ctg atc acc       1056
Arg Gln Gly Tyr Gly Leu Thr Glu Thr Thr Ser Ala Ile Leu Ile Thr
                340                 345                 350 ccc gaa ggg gac gac aag cct ggc gca gta ggc aag gtg gtg ccc ttc       1104
Pro Glu Gly Asp Asp Lys Pro Gly Ala Val Gly Lys Val Val Pro Phe
            355                 360                 365 ttc gag gct aag gtg gtg gac ttg gac acc ggt aag aca ctg ggt gtg       1152
Phe Glu Ala Lys Val Val Asp Leu Asp Thr Gly Lys Thr Leu Gly Val
        370                 375                 380 aac cag cgc ggc gag ctg tgc gtc cgt ggc ccc atg atc atg agc ggc       1200
Asn Gln Arg Gly Glu Leu Cys Val Arg Gly Pro Met Ile Met Ser Gly
385                 390                 395                 400 tac gtt aac aac ccc gag gct aca aac gct ctc atc gac aag gac ggc       1248
Tyr Val Asn Asn Pro Glu Ala Thr Asn Ala Leu Ile Asp Lys Asp Gly
                    405                 410                 415 tgg ctg cac agc ggc gac atc gcc tac tgg gac gag gac gag cac ttc       1296
Trp Leu His Ser Gly Asp Ile Ala Tyr Trp Asp Glu Asp Glu His Phe
                420                 425                 430 ttc atc gtg gac cgg ctg aag agc ctg atc aaa tac aag ggc tac cag       1344
Phe Ile Val Asp Arg Leu Lys Ser Leu Ile Lys Tyr Lys Gly Tyr Gln
            435                 440                 445 gta gcc cca gcc gaa ctg gag agc atc ctg ctg caa cac ccc aac atc       1392
Val Ala Pro Ala Glu Leu Glu Ser Ile Leu Leu Gln His Pro Asn Ile
        450                 455                 460 ttc gac gcc ggg gtc gcc ggc ctg ccc gac gac gat gcc ggc gag ctg       1440
Phe Asp Ala Gly Val Ala Gly Leu Pro Asp Asp Asp Ala Gly Glu Leu
465                 470                 475                 480 ccc gcc gca gtc gtc ctg gaa cac ggt aaa acc atg acc gag aag            1488
Pro Ala Ala Val Val Leu Glu His Gly Lys Thr Met Thr Glu Lys
                    485                 490                 495 gag atc gtg gac tat gtg gcc agc cag gtt aca acc gcc aag aag ctg       1536
Glu Ile Val Asp Tyr Val Ala Ser Gln Val Thr Thr Ala Lys Lys Leu
                500                 505                 510 cgc ggt ggt gtt gtg ttc gtg gac gag gtg cct aaa gga ctg acc ggc       1584
Arg Gly Gly Val Val Phe Val Asp Glu Val Pro Lys Gly Leu Thr Gly
            515                 520                 525 aag ttg gac gcc cgc aag atc cgc gag att ctc att aag gcc aag aag       1632
Lys Leu Asp Ala Arg Lys Ile Arg Glu Ile Leu Ile Lys Ala Lys Lys
        530                 535                 540 ggc ggc aag atc gcc gtg taa                                            1653
Gly Gly Lys Ile Ala Val
```

```
Gly Gly Lys Ile Ala Val
545                 550

<210> SEQ ID NO 4
<211> LENGTH: 550
<212> TYPE: PRT
<213> ORGANISM: Photinus pyralis

<400> SEQUENCE: 4

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365
```

```
Phe Glu Ala Lys Val Val Asp Leu Asp Thr Gly Lys Thr Leu Gly Val
    370             375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
    530                 535                 540
Gly Gly Lys Ile Ala Val
545             550
```

PHARMACEUTICAL COMPOSITION

CROSS-REFERENCE

This application is the US national stage of International Patent Application No. PCT/JP2015/063363 filed on May 8, 2015, which claims priority to Japanese Patent Application No. 2014-097219 filed on May 8, 2014.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
| --- | --- | --- |
| TOD002_Seq_List_20170602.txt | Jun. 2, 2017 | 26 |

TECHNICAL FIELD

The present invention relates to a pharmaceutical composition. More specifically, the present invention relates to a pharmaceutical composition having a micelle form that encapsulates a drug.

BACKGROUND ART

Biological pharmaceuticals that utilize a biopolymer, such as a protein or a nucleic acid, are easily degraded by enzymes or eliminated by the immune system as compared to conventional pharmaceuticals that utilize low-molecular-weight compounds. In order to improve the delivery of such biological drugs to an affected area, drug delivery systems (DDS) have been developed that use polyamino acid-based block copolymers. An aim of this prior work has been to provide a carrier that achieves both stability in blood (retention properties of the biological drugs) and drug-releasing properties in a target cell, and further improvements are required in order to achieve excellent compatibility thereof.

CITATION LIST

Patent Literature 1: JP 2011-140537 A
Patent Literature 2: JP 2002-179683 A

SUMMARY OF THE INVENTION

An object of the present teachings is to provide a carrier and a pharmaceutical composition that can achieve both stability of a biological drug in blood and releasing properties in a target cell.

A pharmaceutical composition according to one embodiment of the present teachings includes:
 a polymer unit α having a hydrophilic polymer chain segment and a cationic polymer chain segment;
 a polymer unit β having a hydrophilic polymer chain segment and a cationic polymer chain segment; and
 a drug,
 in which the polymer unit α and the polymer unit β are radially arranged, such that the cationic polymer chain segments are directed inward and the hydrophilic polymer chain segments are directed outward, and form a micelle, and the drug is encapsulated in the micelle. The cationic polymer chain segment of the polymer unit α has a phenylboronic acid group in a side chain, the cationic polymer chain segment of the polymer unit β has a phenylboronic acid binding site in a side chain, and the phenylboronic acid group and the phenylboronic acid binding site form a cross-linked structure that can dissociate in an acidic environment or in the presence of a substance capable of competitive binding.

In one embodiment thereof, at least one hydrogen of the phenyl ring of the phenylboronic acid group is substituted so as to have a pKa of approximately physiological pH.

In addition or in the alternative, the phenylboronic acid binding site contains a cis-diol structure.

In addition or in the alternative, the drug is a nucleic acid.

In addition or in the alternative, the nucleic acid is pDNA or mRNA.

According to the present invention, a carrier and a pharmaceutical composition are provided that simultaneously achieves stability of a biological drug in blood and releasing properties in a target cell.

DETAILED DESCRIPTION OF THE EMBODIMENTS

Figure 1A:
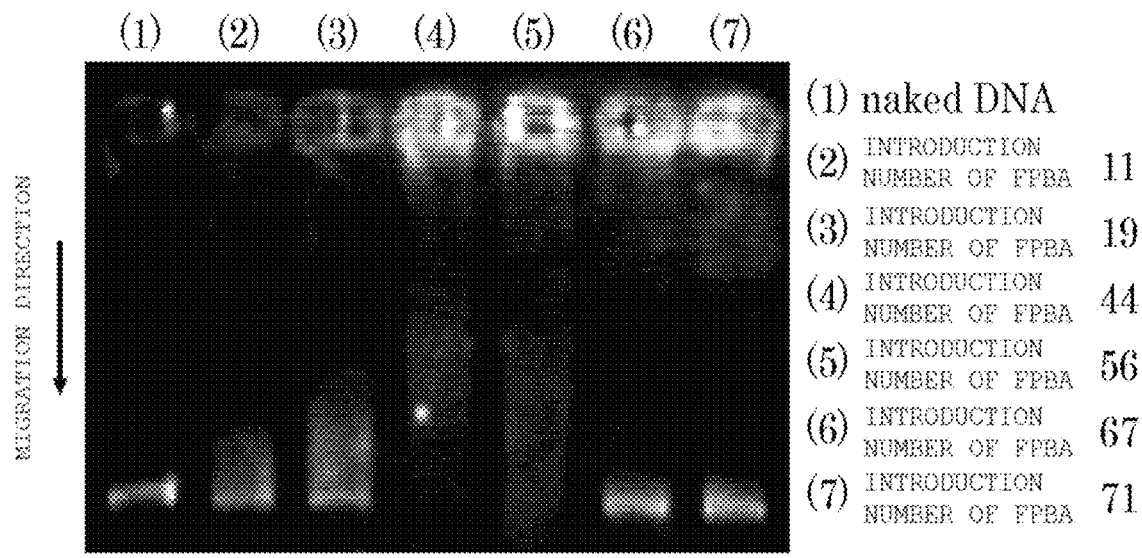
FIG. 1A is an electrophoresis result that compares and shows replacement resistances of a polymer micelle to polyanion for A/P=6 in cases in which the introduction number of polyol structures was fixed at 40 while the introduction number of FPBA groups was varied.

Embodiments of the present invention are described below. However, the present invention is not limited to these embodiments.

A. Synopsis of Pharmaceutical Composition

A pharmaceutical composition according to an embodiment of the present invention includes: a polymer unit α having a hydrophilic polymer chain segment and a cationic polymer chain segment; a polymer unit β having a hydrophilic polymer chain segment and a cationic polymer chain segment; and a drug. The polymer units α and β are radially arranged such that the cationic polymer chain segments are directed inward and the hydrophilic polymer chain segments are directed outward, and form a micelle, and the drug is encapsulated in the micelle. The cationic polymer chain segment of the polymer unit α has a phenylboronic acid group in a side chain, and the cationic polymer chain segment of the polymer unit β has a phenylboronic acid binding site in a side chain. In the micelle, the phenylboronic acid group and the phenylboronic acid binding site form a cross-linked structure that can dissociate in an acidic environment or in the presence of a substance capable of competitive binding. Further details concerning the pharmaceutical composition will now be described.

B. Polymer Unit α

The polymer unit α has a hydrophilic polymer chain segment and a cationic polymer chain segment.

B-1. Hydrophilic Polymer Chain Segment

The hydrophilic polymer chain segment may be formed of any appropriate hydrophilic polymer. Examples of the hydrophilic polymer include poly(ethylene glycol), polysaccharide, poly(vinylpyrrolidone), poly(vinyl alcohol), poly(acrylamide), poly(acrylic acid), poly(methacrylamide), poly(methacrylic acid), poly(methacrylic acid ester), poly(acrylic acid ester), polyamino acid, and poly(malic acid), and derivatives thereof. Specific examples of the polysaccharide include starch, dextran, fructan, and galactan. Of those, poly(ethylene glycol) may be preferably used because: terminal-reactive polyethylene glycols having various functional groups at terminals are commercially available; and polyethylene glycols having various molecular weights are commercially and readily available.

B-2. Cationic Polymer Chain Segment

The cationic polymer chain segment may be constituted of any appropriate cationic polymer. A typical example of the cationic polymer is polyamino acid. The cationic polymer chain segment contains (a) phenylboronic acid (PBA) group(s) in a side chain. In one embodiment, from the viewpoint of compatibility with an in vivo environment typified by blood (less than pH 7.5), in the PBA group, at least one hydrogen atom of the phenyl ring constituting the PBA group is substituted with any substituent so that the phenylboronic acid group has a pKa of approximately physiological pH. The pKa of the substituted PBA group is preferably less than 8, more preferably less than 7.5. When the pKa of the substituted PBA group falls within such range, a cross-linked structure that can dissociate in a desired pH range can be easily formed between the substituted PBA group and the phenylboronic acid (PBA) binding site of the polymer unit β, which will be described below. For example, by controlling the pKa of the substituted PBA group, it is possible to form a cross-linked structure that maintains its structure extracellularly where the pH is about 7 and that easily dissociates intracellularly in late endosomes where the pH is from 5 to 6. The number of substituted hydrogen atoms is 1, 2, 3, or 4. When only one hydrogen atom is substituted, the attachment positions of the substituent and B(OH)$_2$ may be at any one of ortho, meta, and para. Examples of the substituent(s) include: halogens, such as fluorine, chlorine, or bromine; and a nitro group. Of those, from the viewpoint of enhancing hydrophilicity of the block copolymer and from the viewpoint of adjusting the pKa to less than 7.5, the substituted PBA group is preferably a fluorinated phenylboronic acid group represented by the following formula (I) (hereinafter sometimes referred to as "FPBA group"). The pKa of the substituted PBA group is specified from a substituted PBA group-containing amino acid synthesized as a monomer. The lower limit of the pKa of the substituted PBA group is not particularly limited, and for example may be 2 or 3.

[Chem. 1]

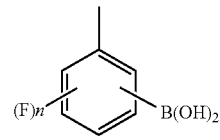

(I)

In formula (I): F('s) is (are) present independently; n is 1, 2, 3, or 4; and when n is 1, the attachment positions of F and B(OH)$_2$ may be at any one of ortho, meta, and para.

Further, when the cationic polymer chain segment of the polymer unit α has the substituted PBA group in a side chain moiety, the following effect can be obtained: an extremely stable polymer micelle can be formed in an aqueous medium (preferably a near-neutral aqueous medium). Specifically, by binding the cationic polymer chain segment having a positive charge with the drug (typically a nucleic acid) having a negative charge via electrostatic interactions, a polymer micelle forms in which the cationic polymer chain segments of the polymer units α and β are inward. In the thus-formed polymer micelle, because the cationic polymer chain segments of the polymer units α and β are brought into proximity with each other, cross-linking between the substituted PBA group(s) of the cationic polymer chain segment of the polymer units α and the PBA binding site(s) of the cationic polymer chain segment of the polymer units β is promoted. As a result, an extremely stable polymer micelle can be formed in an aqueous medium. As described above, in the thus-formed polymer micelle, the polymer unit α (and the polymer unit β that will be described later) is radially arranged with the cationic polymer chain segment directed inward and the hydrophilic polymer chain segment directed outward. Examples of the aqueous medium include water, physiological saline, and aqueous buffers, such as phosphate buffers, carbonate buffers, and Good's buffers.

Now, cationic polymer chain segments (polyamino acid chain segment) constituted of polyamino acids and having, as the PBA group(s), (a) substituted PBA group(s) will be described as representative examples.

The polyamino acid chain segment typically includes (a) cationic group(s) in a side chain, in addition to the PBA group(s). By having (a) cationic group(s) in a side chain moiety of the polyamino acid chain segment, a cationic polymer chain segment forms, and the cationic polymer chain segment can associate with a biopolymer (e.g., a nucleic acid) to form a complex, such as a polyion complex (PIC). Therefore, in one embodiment, the polyamino acid chain segment contains (a) cationic amino acid residue(s) having a cationic group in a side chain and (a) substituted PBA group-containing amino acid residue(s) having a substituted PBA group in a side chain. In this case, the cationic amino acid residue(s) and the substituted PBA group-containing amino acid residue(s) may be different amino acid residues, or may be the same amino acid residue. Specifically, the polyamino acid chain segment may contain a cationic amino acid residue having no substituted PBA group in a side chain and a substituted PBA group-containing amino acid residue having no cationic group in a side chain, or may contain, instead of one or both of, or in addition to, these residues, an amino acid residue having both a cationic group and a substituted PBA group in a side chain.

The cationic amino acid residue(s) is (are) preferably (a) cationic amino acid residue(s) having an amino group in a side chain. By having the amino group(s) in a side chain, the amino group(s) can coordinate with boron(s) of the substituted PBA group(s) in an aqueous medium. As a result, hydrophobization of the polymer unit α due to introduction of the substituted PBA group(s) can be avoided to maintain high hydrophilicity.

As amino acids from which the cationic amino acid residue (s) having an amino group in a side chain is (are) derived, there are given, for example, basic amino acids, such as lysine, ornithine, arginine, homoarginine, or histidine; and amino acid derivatives obtained by introducing any appropriate amine compound into an acidic amino acid. Of those, preferred are lysine and amino acid derivatives obtained by substituting the —OH moiety of a carboxyl group (—C(=O)OH) of an acidic amino acid with any one of the groups of the following formulae (i) to (iv); more preferred are lysine and amino acid derivatives obtained by substituting the —OH moiety of a carboxyl group (—C(=O)OH) at the α-position or β-position of aspartic acid or at the α-position or γ-position of glutamic acid with any one of the groups of the following formulae (i) to (iv); and still more preferred are lysine and amino acid derivatives obtained by substituting the —OH moiety of a carboxyl group (—C(=O) OH) at the α-position or β-position of aspartic acid or at the α-position or γ-position of glutamic acid with the group of the following formula (i):

—NH—(CH$_2$)$_{p1}$—[NH—(CH$_2$)$_{q1}$—]$_{r1}$NH$_2$   (i);

—NH—(CH$_2$)$_{p2}$—N[—(CH$_2$)$_{q2}$—NH$_2$]$_2$   (ii);

—NH—(CH$_2$)$_{p3}$—N{[—(CH$_2$)$_{q3}$—NH$_2$][—(CH$_2$)$_{q4}$—NH—]$_{r2}$H}   (iii); and —NH—(CH$_2$)$_{p4}$—N{—(CH$_2$)$_{q5}$—N[—(CH$_2$)$_{q6}$—NH$_2$]$_2$}$_2$   (iv)

in formulae (i) to (iv): p1 to p4, q1 to q6, and r1 and r2 each are independently an integer of from 1 to 5.

In formulae (i) to (iv), p1 to p4 and q1 to q6 each are independently preferably 2 or 3, more preferably 2. In addition, r1 and r2 are each independently an integer of from 1 to 3.

In case the cationic amino acid residue is (are) (a) lysine residue(s), there are advantages in that the polyamino acid chain is easily synthesized and the resultant block copolymer exceedingly excels in biocompatibility. In addition, it has been demonstrated that, in case the cationic amino acid residue (s) is (are) (an) amino acid residue (s) obtained by substituting the —OH moiety of a carboxyl group (—C(=O) OH) of an acidic amino acid with any one of the groups of formulae (i) to (iv), because the residues have a plurality of different amine functional groups, they exhibit a plurality of stages of pKa's, a plurality of amine functional groups are partially protonated under physiological conditions at pH 7.4 and damage to cells is low. In addition, there is an advantage in that interactions with nucleic acids or the like enable suitable formation of a complex, such as a PIC. Further, when the complex thus formed is internalized into an endosome (pH 5.5) and the pH decreases, the protonation of the polyamino acid chain segment further proceeds, and endosomal escape may be promoted based on a buffer effect (or a proton sponge effect) or enhanced membrane-damaging activity. As a result, it is possible to improve the efficiency of the drug delivery to the cytoplasm.

The substituted PBA group is typically introduced into the side chain of the substituted PBA group-containing amino acid residue via a linking group. Examples of the linking group include an amide bond, a carbamoyl bond, an alkyl bond, an ether bond, an ester bond, a thioester bond, a thioether bond, a sulfonamide bond, a urethane bond, a sulfonyl bond, a thymine bond, a urea bond, and a thiourea bond, and combinations thereof. The linking group may contain any appropriate spacer between those bonds. Examples of the spacer include: a linear or branched alkylene group having 1 to 27 carbon atoms, preferably 2 to 5 carbon atoms; and a short-chain of ethylene glycol (—OCH$_2$CH$_2$-)$_n$.

As amino acid residues into which the substituted PBA group is introduced, any appropriate amino acid residue may be selected as long as the substituted PBA group is introduced via the linking group. From the viewpoint of ease of synthesis, the substituted PBA group is preferably introduced into a cationic amino acid residue having an amino group in a side chain. As a specific example, the substituted PBA group may be introduced into the cationic amino acid residue having an amino group in a side chain via an amide bond formed by reaction of the amino group with carboxyphenylboronic acid, in which at least one hydrogen atom of a phenyl ring has been substituted, or an ester thereof. As another specific example, the substituted PBA group may be introduced into the amino group of a cationic amino acid residue having an amino group in a side chain via a linking group formed of two amide bonds and a propylene group included therebetween. In this context, only one substituted PBA group or a plurality of substituted PBA groups may be introduced into a cationic amino acid residue having a plurality of amino groups in a side chain. In case only one substituted PBA group is introduced, the substituted PBA group-containing amino acid residue obtained by the introduction has both the amino group and the substituted PBA group in the side chain, and hence is also a cationic amino acid residue. Therefore, in the present invention, a polyamino acid chain segment containing only such amino acid residues is also understood to include both the cationic amino acid residue and the substituted PBA group-containing amino acid residue. However, in determining the sum of the number of cationic amino acid residues and the number of substituted PBA group-containing amino acid residues in the polyamino acid chain segment containing such amino acid residue, the amino acid residues are counted as any one of the cationic amino acid residues and the substituted PBA group-containing amino acid residues.

The polyamino acid chain segment may further include (an) amino acid residue(s) having a hydrophobic group in a side chain (hereinafter sometimes referred to as "hydrophobic amino acid residue") as well as the cationic amino acid residue(s) and the substituted PBA group-containing amino acid residue(s). By including the hydrophobic amino acid residue(s), in an aqueous medium, hydrophobic interactions among the polymer units α increase. As a result, a more stable polymer micelle may be formed. Further, the hydrophobic amino acid residue(s) stick(s) into hydrophobic moieties on the cell membrane and can function as an anchor for fixing the polymer micelle to the cell membrane. Therefore, in case a biopolymer, such as a nucleic acid, is encapsulated in the polymer micelle, the introduction rate of the biopolymer into cells can be increased.

Amino acids from which the hydrophobic amino acid residue is derived are preferably exemplified by amino acids having a solubility of 5 g or less in 100 g of water at 25° C., more preferably 4 g or less. Examples of such amino acids include non-polar natural amino acids, such as leucine, isoleucine, phenylalanine, methionine, or tryptophan, and hydrophobic derivatives of amino acids that have a hydrophobic group introduced into a side chain. As the hydrophobic derivative of the amino acid, there is preferably given derivatives that have a hydrophobic group introduced into a side chain of an acidic amino acid, e.g., aspartic acid or glutamic acid, a side chain of an acidic amino acid having an amine compound introduced therein, or a side chain of a basic amino acid, e.g., lysine, ornithine, arginine, homoarginine, or histidine.

The hydrophobic group to be introduced preferably may be exemplified by saturated or unsaturated, linear or branched, aliphatic hydrocarbon groups having 6 to 27 carbon atoms, aromatic hydrocarbon groups having 6 to 27 carbon atoms, or steryl groups (residues derived from a steroid).

Examples of saturated, linear or branched, aliphatic hydrocarbon groups having 6 to 27 carbon atoms include a hexyl group (e.g., a n-hexyl group), a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, an eicosyl group, a henicosyl group, a heneicosyl group, a docosyl group, a tricosyl group, a tetracosyl group, a pentacosyl group, a hexacosyl group, and a heptacosyl group. Example of unsaturated, linear or branched, aliphatic hydrocarbon groups having 6 to 27 carbon atoms are groups in which 1 to 5 carbon-carbon single bonds in a chain of any of the alkyl groups given above are replaced with carbon-carbon double bonds.

Examples of aromatic hydrocarbon groups having 6 to 27 carbon atoms include an aryl group and an aralkyl group. Preferred specific examples of those groups include a phenyl group, a naphthyl group, a tolyl group, a xylyl group, a benzyl group, and a phenethyl group.

An example of the steroid from which the steryl group is derived are sterols. Sterols mean natural, semisynthetic, or synthetic compounds based on a cyclopentanone hydrophenanthrene ring ($C_{17}H_{28}$) and derivatives thereof. For example, natural sterols are exemplified by, but not limited to, cholesterol, cholestanol, dihydrocholesterol, cholic acid, campesterol, or sitosterol. Semisynthetic or synthetic compounds thereof may be, for example, synthetic precursors of those natural products (as necessary, encompassing compounds in which part or all of, if present, certain functional groups, hydroxy groups have been protected with a hydroxy protective group known in the art, or compounds in which a carboxyl group has been protected with a carboxyl protective group). In addition, sterol derivatives mean that, for example, without adversely affecting the object of the present invention, a $C_{1-12}$ alkyl group or a halogen atom, such as chlorine, bromine, or fluorine, may be introduced into the cyclopentanone hydrophenanthrene ring, and the ring system may be saturated or partially unsaturated. Sterols from which the steryl group is derived are preferably a sterol originating from an animal or vegetable oil, such as cholesterol, cholestanol, dihydrocholesterol, cholic acid, campesterol, or sitosterol, more preferably cholesterol, cholestanol, or dihydrocholesterol, particularly preferably cholesterol.

The polyamino acid chain segment may include, as each of the cationic amino acid residue(s), the substituted PBA group-containing amino acid residue(s), and the hydrophobic amino acid residue(s), only one type of amino acid residue or two or more types of amino acid residues. In addition, the binding order of the cationic amino acid residue(s), the substituted PBA group-containing amino acid residue(s), and the hydrophobic amino acid residue(s) in the polyamino acid chain segment is arbitrary, and it may be a random structure or a block structure.

The number of the cationic amino acid residue(s), the substituted PBA group-containing amino acid residue(s), and the hydrophobic amino acid residue(s) contained in the polyamino acid chain segment may be appropriately adjusted depending on the type of each of the amino acid residues, or the like.

B-3. Specific Examples of Block Copolymers Capable of Constituting Polymer Unit α

Specific examples of block copolymers capable of constituting the polymer unit α are represented by formulae (1) and (2). In the block copolymers of formulae (1) and (2), the substituted PBA group(s) is (are) introduced into the side chain(s) of the cationic amino acid residue(s). The substituted PBA group(s) may be typically introduced through a reaction with a $Q_1$ moiety, or with an $R^{6a}$ and/or $R^{6b}$ moiety of the block copolymers of formulae (1) and (2):

[Chem. 2]

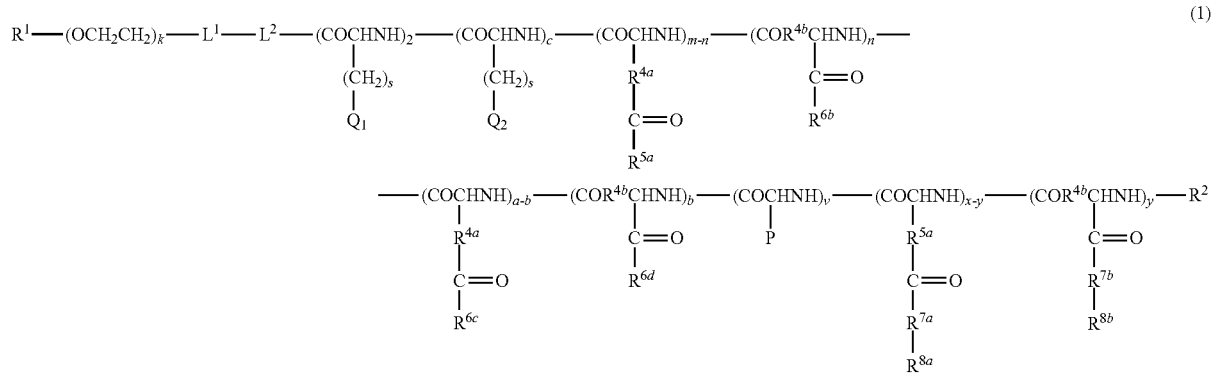

(1)

-continued

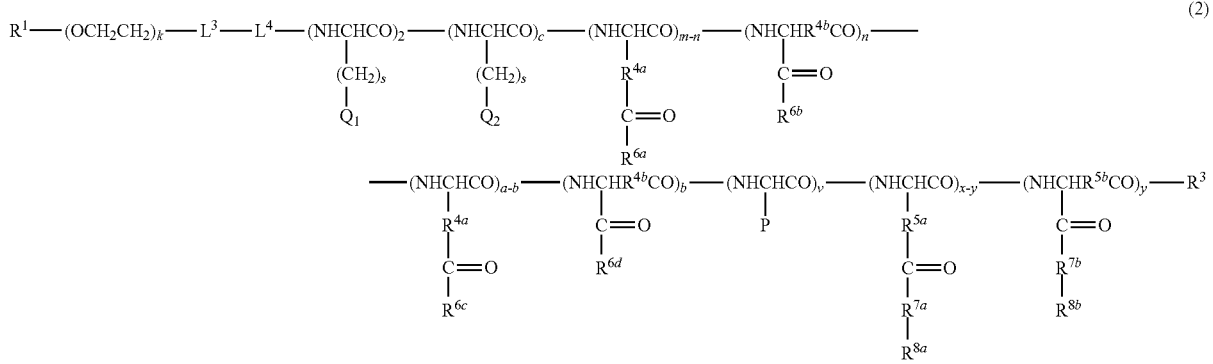

(2)

in formulae (1) and (2):

the $R^1$ group is a hydrogen atom or an unsubstituted or substituted, linear or branched, alkyl group having 1 to 12 carbon atoms;

the $R^2$ group is a hydrogen atom, an unsubstituted or substituted, linear or branched, alkyl group having 1 to 12 carbon atoms, or an unsubstituted or substituted, linear or branched, alkylcarbonyl group having 1 to 24 carbon atoms;

the $R^3$ group is a hydroxyl group, an unsubstituted or substituted, linear or branched, alkyloxy group having 1 to 12 carbon atoms, an unsubstituted or substituted, linear or branched, alkenyloxy group having 2 to 12 carbon atoms, an unsubstituted or substituted, linear or branched, alkynyloxy group having 2 to 12 carbon atoms, or an unsubstituted or substituted, linear or branched, alkyl-substituted imino group having 1 to 12 carbon atoms;

the $R^{4a}$, $R^{4b}$, $R^{5a}$, and $R^{5b}$ groups are each independently a methylene group or an ethylene group;

the $R^{6a}$ and $R^{6b}$ groups are each independently a group selected from groups of the above-described formulae (i) to (iv);

the $R^{6c}$ and $R^{6d}$ groups are each independently a group obtained by introducing a saturated or unsaturated, linear or branched, aliphatic hydrocarbon group having 6 to 27 carbon atoms, an aromatic hydrocarbon group having 6 to 27 carbon atoms, or a steryl group into an amino group of a group selected from groups of the above-described formulae (i) to (iv);

the $R^{7a}$ and $R^{7b}$ groups are each independently —O— or —NH—; the $R^{8a}$ and $R^{8b}$ groups are each independently a saturated or unsaturated, linear or branched, aliphatic hydrocarbon group having 6 to 27 carbon atoms, an aromatic hydrocarbon group having 6 to 27 carbon atoms, or a steryl group;

the $Q_1$ group is —NH$_2$, —NHC(=NH)NH$_2$, or a group represented by the following formula (II),

[Chem. 3]

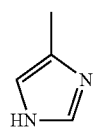

(II)

the $Q_2$ group is a group, in which a saturated or unsaturated, linear or branched, aliphatic hydrocarbon group having 6 to 27 carbon atoms, an aromatic hydrocarbon group having 6 to 27 carbon atoms, or a steryl group is introduced into an (the) amino group of —NH$_2$, —NHC(=NH)NH$_2$, or the group represented by the above-described formula (II);

the P group is a side chain of leucine, isoleucine, phenylalanine, methionine, or tryptophan;

$L^1$ and $L^3$ are each independently —S—S— or a valence bond;

$L^2$ is —NH—, —O—, —O(CH$_2$)$_{p1}$—NH—, or -$L^{2a}$-(CH$_2$)$_{q1}$-$L^{2b}$-, where p1 and q1 are each independently an integer of from 1 to 5, $L^{2a}$ is OCO, OCONH, NHCO, NHCOO, NHCONH, CONH, or COO, and $L^{2b}$ is NH or O;

$L^4$ is —OCO—(CH$_2$)$_{p2}$—CO—, —NHCO—(CH$_2$)$_{p3}$—CO—, or -$L^{4a}$-(CH$_2$)$_{q2}$—CO—, where p2, p3, and q2 are each independently an integer of from 1 to 5, and $L^{4a}$ is OCONH, —CH$_2$NHCO—, NHCOO, NHCONH, CONH, or COO;

k is an integer of from 30 to 20,000;
s is an integer of from 1 to 6;
m is an integer of from 0 to 300;
n is an integer of from 0 to m;
a is an integer of from 0 to 300;
b is an integer of from 0 to a;
v is an integer of from 0 to 300;
c is an integer of from 0 to 300;
x is an integer of from 0 to 300;
y is an integer of from 0 to x;
z is an integer of from 0 to 300;
with the proviso that,
when m is 0, z is an integer of 2 or more;
when z is 0, m is an integer of 1 or more; and when the sum of the total number of primary amino groups and secondary amino groups contained in z of the $Q_1$ group and the total number of primary amino groups and secondary amino groups contained in (m-n) of the $R^{6a}$ group and n of the $R^{6b}$ group, is defined as w, 1 or more but less than w of the hydrogen atom(s) of the amino group(s) is (are) each substituted with an organic group (e.g., an acyl group) having a substituted PBA group (e.g., an FPBA group represented by the formula (I)).

In formula (1) or (2), both of $L^1$ and $L^2$ and both of $L^3$ and $L^4$ each need to be combined together so as to form one linking group. For example, when $L^2$ is —NH—, $L^1$ is not —S—S— but rather is a valence bond.

In formula (1) or (2), k, which represents the number of repetitions of ethylene glycol (or oxyethylene), is an integer of from 30 to 20,000, preferably from 40 to 2,000, more preferably from 50 to 1,500.

An alkyl moiety in the linear or branched alkyloxy group, alkyl-substituted imino group, and alkyl group having 1 to 12 carbon atoms, which are defined by the $R^1$ to $R^3$ groups, may be, for example, a methyl group, an ethyl group, a n-propyl group, an isopropyl group, a n-butyl group, a sec-butyl group, a tert-butyl group, a n-hexyl group, a decyl group, and an undecyl group. An alkenyl or alkynyl moiety in the linear or branched alkenyloxy group having 2 to 12 carbon atoms or the linear or branched alkynyloxy group having 2 to 12 carbon atoms may be exemplified by an alkenyl or alkynyl moiety containing a double bond or a triple bond in the alkyl group having 2 or more carbon atoms as exemplified above.

For such groups or moieties, substituents in a "substituted" case may be exemplified by, but not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkyl siloxy group, a siloxy group, or a silylamino group, or may be exemplified by an acetalized formyl group, a formyl group, or a halogen atom, such as chlorine or fluorine. In this context, for example, the expression "$C_{1-6}$" means 1 to 6 carbon atoms and is used with the same meaning in the following description. Further, an unsubstituted or substituted, linear or branched, alkyl moiety having 1 to 12 carbon atoms in the unsubstituted or substituted, linear or branched, alkylcarbonyl group having 1 to 24 carbon atoms may be selected with reference to the above-described examples, and an alkyl moiety having 13 or more carbon atoms may be, for example, a tridecyl group, a tetradecyl group, a pentadecyl group, a nonadecyl group, a docosanyl group, or a tetracosyl group.

In another embodiment, a substituent for the $R^1$ group may be a group containing a target binding site. The introduction of the target binding site into the terminus of a polymer can improve the delivery of a drug (e.g., a nucleic acid) to a desired target site. The group containing the target binding site may be any appropriate group as long as the group has targeting properties or functionality for a tissue to be targeted; for example, the group may be a group originating from a physiologically active substance, such as an antibody or a fragment thereof, or another protein or peptide each having functionality or targeting properties, a peptide, an aptamer, a sugar such as lactose, or folic acid, and derivatives thereof.

An example of the $R^1$ group substituted by a group including the target binding site is represented by the following formula (III):

[Chem. 4]

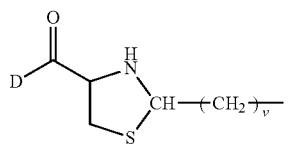

(III)

where v represents an integer of from 1 to 5, and D represents the target binding site.

D is preferably a peptide having a weight average molecular weight of from 50 to 20,000, more preferably a peptide having a weight average molecular weight of from 100 to 10,000, still more preferably a peptide having a weight average molecular weight of from 150 to 3,000.

In addition, D is preferably a peptide having 1 to 200 amino acid residues, more preferably a peptide having 1 to 100 amino acid residues, still more preferably a peptide having 1 to 30 amino acid residues.

Examples of the peptide include peptides capable of specifically binding to integrin, which is involved in angiogenesis, intimal thickening, and malignant tumor growth, and specific examples thereof include RGD peptides. By using an RGD peptide as the target binding site, particles, which are capable of specifically recognizing a diseased portion, and pharmaceutical compositions using the particles are obtainable. The RGD peptides as used herein refer to peptides that include an arginine-glycine-aspartic acid (RGD) sequence. The RGD peptide is preferably a cyclic RGD (cRGD) peptide. Specifically, D may be represented by the following formula (IV).

[Chem. 5]

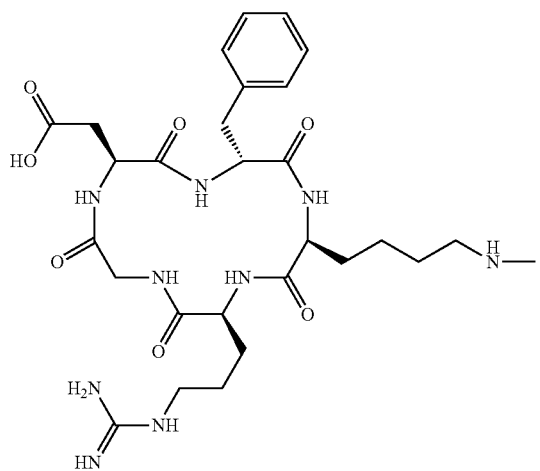

(IV)

The groups of formulae (i) to (iv) and the hydrocarbon group or steryl group defined in formula (1) or (2) are as mentioned above. For the $Q_1$, $Q_2$, $R^{6a}$, $R^{6b}$, $R^{6c}$, $R^{6d}$, $R^{8a}$, and $R^{8b}$ groups, the same group may be selected for all of repeating units belonging thereto, or different groups may be selected. In addition, s is, for example, 1, 3, or 4.

The hydrophobic group to be introduced into the $Q_2$, $R^{6c}$, or $R^{6d}$ group may be introduced via any appropriate linking group. Specific examples of the linking group include the ones described above as the linking groups applicable to the introduction of the substituted PBA group(s).

In formula (1) or (2), in case both of the $R^{4a}$ and $R^{4b}$ groups represent an ethylene group, typically polyamino acids are represented in which n and b each represent an integer of 0 or in which m-n and a-b each represent an integer of 0. The former represents, for example, poly-α-glutamic acid, which is obtained by the polymerization of an N-carboxylic anhydride of glutamic acid γ-benzyl ester, and the latter represents, for example, poly-γ-glutamic acid, which strains of the bacteria genus *Bacillus* such as *Bacillus natto* produce. On the other hand, in case both of the $R^{4a}$ and $R^{4b}$ groups represent a methylene group, it is understood that the respective repeating units having those groups may coexist with each other. The same holds true for the $R^{5a}$ and $R^{5b}$ groups in formula (1) or (2). From the viewpoint of manufacturing efficiency, it is preferred that the $R^{4a}$ and $R^{4b}$ groups are methylene groups and the $R^{5a}$ and $R^{5b}$ groups are ethylene groups.

The total number of cationic amino acid residues and substituted PBA group-containing amino acid residues contained in the polyamino acid chain segment constituting the polymer unit α is 1 or more. From the viewpoint of the stability of the polymer micelle that will be formed, the total number of cationic amino acid residues and substituted PBA group-containing amino acid residues is an integer of preferably 10 or more, more preferably 20 or more (for example, an integer of 30 or more, 40 or more, or 50 or more), and is an integer of preferably 300 or less, more preferably 200 or less, still more preferably 150 or less, yet still more preferably 100 or less. When the polyamino acid chain segment contains a hydrophobic amino acid residue, the number of cationic amino acid residues may be appropriately adjusted within the above-mentioned suitable range depending on the number of hydrophobic amino acid residues. When the polyamino acid chain segment contains a hydrophobic amino acid residue, the micelle can become more stabilized. Accordingly, the total number of cationic amino acid residues, substituted PBA group-containing amino acid residues, and hydrophobic amino acid residues may be an integer of preferably from 10 to 150, more preferably from 20 to 100.

In the polyamino acid chain segment constituting the polymer unit α, the number of substituted PBA group-containing amino acid residues may be appropriately adjusted depending on, for example, the type or number of cationic amino acid residue (s). Specifically, as long as the polymer micelle can be stably formed, the number or introduction ratio of substituted PBA group-containing amino acid residues may be set to any appropriate value. For example, the introduction ratio of the substituted PBA group-containing amino acid residue (number of substituted PBA group-containing amino acid residues with respect to the total number of cationic amino acid residues in the polymer unit α) is preferably 1% or more, more preferably 5% or more, still more preferably 10% or more, and is preferably 90% or less, more preferably 80% or less, still more preferably 70% or less (when the polyamino acid chain segment contains no hydrophobic amino acid residue, the introduction ratio may be, for example, from 30% to 90%, from 40% to 80%, or from 50% to 70%). When the introduction ratio of the substituted PBA group-containing amino acid residue falls within such range, cross-linked structures having a desired cross-link density are formed, and as a result, a polymer micelle that excels in stability and drug retention properties in blood, and that excels in dissociation and drug releasing properties in cells, can be achieved.

[B-4. Production Method for Polymer Unit α]

In one embodiment, the polymer unit α may be produced by any appropriate synthesis method. An example of the synthesis method for the polymer unit α in one embodiment is as described below. The polymer unit α may be produced by: forming a polyethylene glycol chain by anion living polymerization using an initiator capable of providing $R^1$; introducing an amino group at the growing end side of the polyethylene glycol chain; from the amino end, polymerizing a protected amino acid derivative, such as NCA-Lys (TFA), to form a polyamino acid chain segment; deprotecting the side chains of the polyamino acids to expose the amino groups; and subjecting the exposed amino groups to a reaction with the carboxyl group of a fluorinated carboxyphenylboronic acid to introduce a desired number of FPBA groups into the side chain(s) via amide bond(s).

In another embodiment, the polymer unit α may be produced as described below, for example. The polymer unit α may be produced by: forming a polyethylene glycol chain by anion living polymerization using an initiator capable of providing $R^1$; introducing an amino group at the growing end side of the polyethylene glycol chain; from the amino end, polymerizing an N-carboxylic anhydride of a protected amino acid, such as β-benzyl-L-aspartate or γ-benzyl-L-glutamate, to form a polyamino acid chain segment; subsequently subjecting the polyamino acid to a reaction with an amine compound, such as diethylenetriamine (DET), to introduce (an) amine residue(s), such as a DET group, into the amino acid side chain(s) by an ester-amide exchange reaction; and subsequently subjecting amino groups of the amine residues to a reaction with the carboxyl group of a fluorinated carboxyphenylboronic acid to introduce a desired number of FPBA groups into the side chain via (an) amide bond(s). In this case, if the polyamino acid chain segment is formed by combining β-benzyl-L-aspartate and γ-benzyl-L-glutamate, the subsequent ester-amide exchange reaction occurs preferentially for β-benzyl-L-aspartate. As a result, a block copolymer may be obtained that includes (an) amino acid residue(s) originating from γ-benzyl-L-glutamate as the hydrophobic amino acid residue(s).

It should be noted that a portion of the amino acid ester residues may undergo a structural change by nucleophilic attack of an amine (for example, imide ring formation through the dealcoholization of an amino acid ester residue) during the synthesis process. The polyamino acid chain segment to be used in the present invention may further include residues that have undergone such structural change. In this case, the residues that have undergone the structural change are excluded from the cationic amino acid residue, the substituted PBA group-containing amino acid residue, and the hydrophobic amino acid residue. In addition, a portion of the NH groups and $NH_2$ groups in the cationic amino acid residues may be converted into (a) salt(s) (mainly hydrochloride) by use of an acid (mainly hydrochloric acid) during the synthesis process. In the present invention, the polyamino acid chain segment may include such structure(s). In other words, a portion of the NH groups and $NH_2$ groups in the Q, $R^{6a}$, and $R^{6b}$ groups may be in the form of a salt (for example, hydrochloride).

In addition, a block copolymer including a hydrophilic polymer (polyethylene glycol) having a target binding site at the end may be synthesized by: synthesizing a block copolymer as mentioned above using polyethylene glycol having a target binding site at the α-end or synthesizing a block copolymer as mentioned above using polyethylene glycol having a functional group capable of subsequently introducing a group including a target binding site into the α-end; and then introducing the group including the target binding site. A variety of methods may be used as introduction methods for the group including the target binding site; for example, by mixing in an acidic solution a block copolymer, which has a polyethylene glycol chain acetalized at the α-end, and a compound, which has a desired target binding site and a cysteine terminus, the target binding site can be provided at the terminus of the polyethylene glycol chain.

C. Polymer Unit β

The polymer unit β has a hydrophilic polymer chain segment and a cationic polymer chain segment like the polymer unit α. The hydrophilic polymer chain segment is as described in section B-1 for the polymer unit α. Hereinafter, only the characteristic portions of the polymer unit β will be described for the cationic polymer chain segment of the polymer unit β. With regard to the other portions, it is as described in the section B-2 for the polymer unit α.

The cationic polymer chain segment of the polymer unit β has a PBA binding site in a side chain. Any appropriate chemical structure capable of binding to a PBA group to form a cross-linked structure may be adopted as the PBA binding site. Examples of chemical structures capable of constituting the PBA binding site include a polyol (in particular, a cis-diol), a diamine, hydroxyamine, a hydroxamic acid, and an alkoxycarboxyamide. The reaction between the PBA binding site and the PBA group is typically a dehydration reaction, and hence the binding between the PBA binding site and the PBA group is typically a covalent bond. As compounds having a chemical structure capable of serving as the PBA binding site, for example, the following compounds 1 to 43 and derivatives thereof can be mentioned.

[Chem. 6]

1
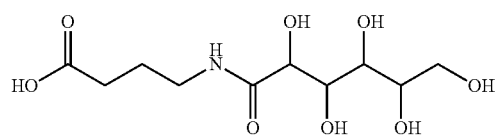

[Chem. 7]

2
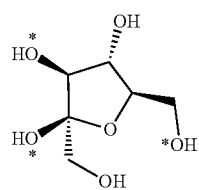

3
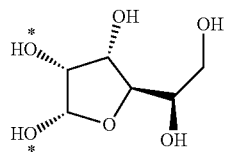

4
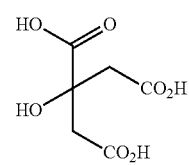

5
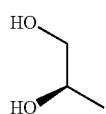

6
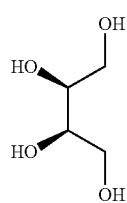

7
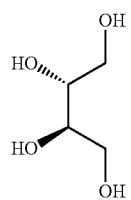

8
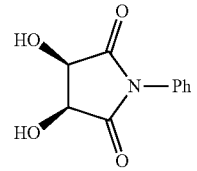

9
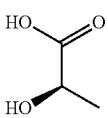

10
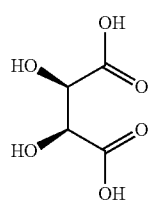

11
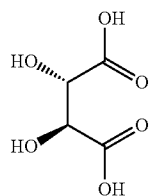

12
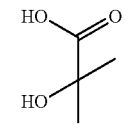

13
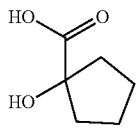

14
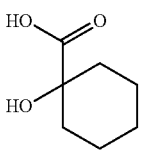

15

[Chem. 8]
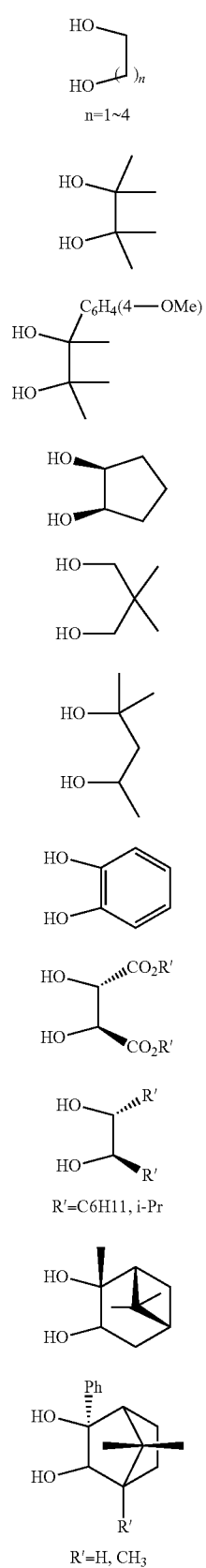
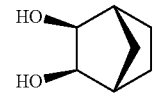
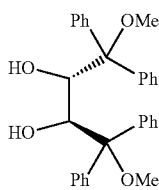
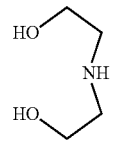
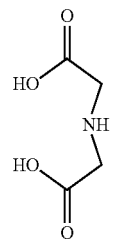
[Chem. 9]
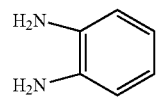
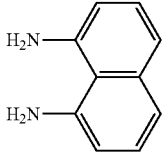
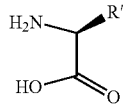
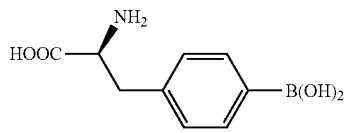
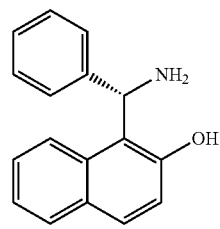

-continued

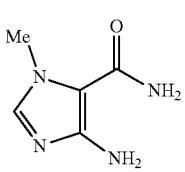
36

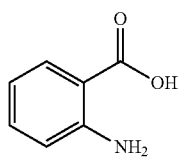
37

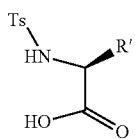
38

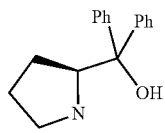
39

[Chem. 10]

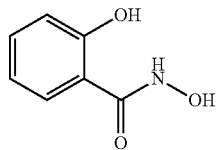
40

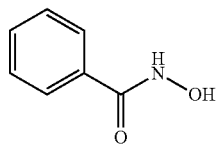
41

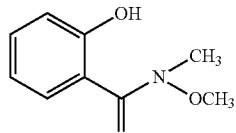
42

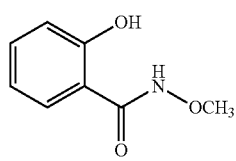
43

A functional group (e.g., a carboxyl group) capable of reacting with an amino group may be introduced into any appropriate position of any such compound as described above through the use of any appropriate reaction. The introduction of such a functional group facilitates a reaction with an amino group in a side chain of the cationic polymer chain segment, and as a result, facilitates the introduction of the PBA binding site.

In case the PBA binding site is a polyol structure, the number of hydroxy groups contained in a polyol compound from which the polyol structure is derived may be appropriately selected according to the objective, etc. The polyol structure preferably contains a cis-diol structure. Because the cis-diol structure easily forms an ester bond between itself and a PBA group, an ester bond is easily formed between the PBA group of the polymer unit α and the polyol structure of the polymer unit β. As a result, a very stable polymer micelle can be formed. In addition, as described above, for example, a carboxyl group may be introduced into any appropriate position of the polyol compound through the use of any appropriate reaction. The introduction of the carboxyl group facilitates a reaction with a side chain of the cationic polymer chain segment (substantially, an amino group in the side chain), and as a result, facilitates the introduction of the polyol structure. From such viewpoint, compound 1 (a gluconic acid derivative) is preferred. In addition, polyol structures derived from such a compound also excels in reactivity with the PBA group of the polymer unit α, and hence can form the desired cross-linked structure.

Methods of introducing the PBA binding site (e.g., a polyol structure) into the polymer unit β are similar to the methods of introducing the PBA group into the polymer unit α. For example, an amino group in a side chain of a polyamino acid chain segment in a block copolymer having a polyethylene glycol (PEG) chain segment and a polyamino acid chain segment may be subjected to a reaction with a carboxyl group of a compound having the PBA binding site (e.g., a polyol compound, such the gluconic acid derivative that is the compound 1) to introduce a polyol structure(s) into the side chain. The structures of the main chain and side chain of the block copolymer before the introduction of the PBA binding site(s) are similar to the structures of the main chain and side chain of the block copolymer before the introduction of the PBA group(s), and hence reference may be made to the description for the polymer unit α in sections B-2 to B-4.

As described above, the block copolymer capable of constituting the polymer unit β is similar to the block copolymer capable of constituting the polymer unit α, and specific examples thereof are the block copolymers represented by the formulas (1) and (2) (with the proviso that when the sum of the total number of primary amino groups and secondary amino groups contained in z of group $Q_1$ and the total number of primary amino groups and secondary amino groups contained in (m-n) of $R^{6a}$ group and n of $R^{6b}$ group is defined as w, 1 or more but less than w of the hydrogen atoms of the amino groups are each substituted with a residue having the PBA binding site). The total number of cationic amino acid residues and PBA binding site-containing amino acid residues contained in the polyamino acid chain segment constituting the polymer unit β is similar to that in the case of the polymer unit α. Specifically, the total number is an integer of 1 or more, preferably 10 or more, more preferably 20 or more (for example, an integer of 30 or more, 40 or more, or 50 or more), and is an integer of preferably 300 or less, more preferably 200 or less, still more preferably 150 or less, yet still more preferably 100 or less. When the polyamino acid chain segment contains a hydrophobic amino acid residue, the number of cationic amino acid residues may be appropriately adjusted within the above-mentioned suitable range depending on the number of hydrophobic amino acid residues. When the polyamino acid chain segment contains (a) hydrophobic amino acid residue(s), the micelle can become more stabilized. Accordingly, the total number of cationic amino acid residues, PBA binding site-containing amino acid residues, and hydrophobic amino acid residues may be preferably from 10 to 150, more preferably from 20 to 100.

In the polyamino acid chain segment constituting the polymer unit β, the number of PBA binding site-containing amino acid residues may be appropriately adjusted depending on, for example, the type or number of cationic amino acid residues. Specifically, as long as the polymer micelle can be stably formed, the number or introduction ratio of PBA binding site-containing amino acid residues may be set to any appropriate value. For example, the introduction ratio of the PBA binding site-containing amino acid residue (number of PBA group binding site-containing amino acid residues with respect to the total number of cationic amino acid residues in the polymer unit β) is preferably 1% or more, more preferably 5% or more, still more preferably 10% or more, and is preferably 90% or less, more preferably 80% or less, still more preferably 70% or less (when the polyamino acid chain segment contains no hydrophobic amino acid residue, the introduction ratio may be, for example, from 30% to 90%, from 40% to 80%, or from 50% to 70%). When the introduction ratio of the PBA binding site-containing amino acid residue falls within such range, cross-linked structures having a desired cross-link density are formed. As a result, a polymer micelle that excels in stability and drug retention properties in blood, and that excels in dissociation and drug releasing properties in cells can be achieved.

D. Polymer Micelle and Cross-Linked Structure

D-1. Polymer Micelle

As described above, in the pharmaceutical composition according to the embodiment of the present invention, the polymer units α and β form a polymer micelle by being radially arranged so that the cationic polymer chain segments are directed inward and the hydrophilic polymer chain segments are directed outward. The average particle diameter of the polymer micelle is preferably from 20 nm to 200 nm, more preferably from 30 nm to 150 nm, still more preferably from 30 nm to 120 nm.

The contents of the polymer units α and β in the polymer micelle only need to be such that the charge ratio of cations of the polymer units α and β to anions of the drug is 1 or more. For example, in case the drug is a nucleic acid, the polymer micelle may have a ratio [number of positive charges of the cationic polymer chain segment]/[number of negative charges of the nucleic acid] at a pH of 7.4 of, for example, from 1/1 to 20/1, preferably from 1/1 to 10/1. The ratio between the contents of the polymer unit α and the polymer unit β in the polymer micelle is preferably from 2:3 to 3:2, more preferably around 1:1.

D-2. Cross-Linked Structure

Figure 8:
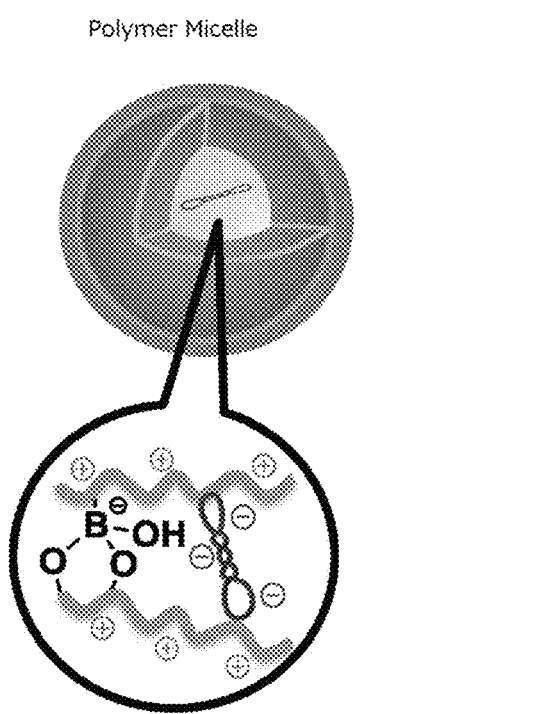
FIG. 8 schematically shows a drug encapsulated in a polymer micelle according to one aspect of the present teachings.

In the polymer micelle, the phenylboronic acid group(s) of the polymer units α and the PBA binding site (s) of the polymer units β form cross-linked structures as shown in FIG. 8 and described below. It is noted that FIG. 8 schematically shows the drug encapsulated in the polymer micelle as well as the cross-linked structure.

The cross-linked structure shown in FIG. 8 can dissociate in an acidic environment, preferably at a pH of 6 or less, more preferably at a pH in the range of from 4 to 6. By forming such cross-linked structure, a high drug (e.g., nucleic acid) delivery capability to cells can be achieved. Specifically, in vivo, the extracellular pH is about 7, whereas intracellularly the pH of late endosomes is from 5 to 6. Therefore, the cross-linked structure maintains the structure extracellularly, and easily dissociates intracellularly in late endosomes. As a result, the pharmaceutical composition (e.g., a polymer micelle) according to an embodiment of the present invention can stably maintain a drug (e.g., nucleic acid)-encapsulating form until reaching a target cell, and can smoothly and efficiently release the drug into the target cell after being taken up by the target cell. More specifically, the release of the drug can be achieved as described below. The polymer micelle taken up by the target cell undergoes dissociation of the cross-linked structure in the acidic environment (typically having a pH of from 5 to 6) in a late endosome. As a result, polymer units having a relatively strong interaction with the drug associate. On the other hand, polymer units having a relatively weak interaction with the drug break away from the micelle, and the drug achieves endosomal escape by exhibiting membrane-damaging activity on the endosomal membrane. The electrostatic binding and hydrophobic interaction of the drug (e.g., nucleic acid) aggregates within the cytoplasm are weakened by the action of adenosine triphosphate (ATP) present at high concentration in cytoplasm; similarly, the drug can be released into cells by a replacement reaction with anionic substances, such as nucleic acids or proteins, present at high concentration in cytoplasm as well. In some cases, the cross-linked structure dissociates in the presence of a substance capable of competitive binding. As used herein, the term "substance capable of competitive binding" refers to substances having a functional group that can form a bond between itself and the PBA group or the PBA binding site more easily than that of the bond (cross-linked structure) between the PBA group and the PBA binding site. That is, in the presence of such a substance, the PBA group or the PBA binding site preferentially binds to the functional group of the substance, and thus the cross-linked structure can dissociate. The mechanism of drug release after the dissociation of the cross-linked structure is the same as above. Specific examples of substances capable of competitive binding include ribonucleotides or ribonucleosides, such as RNA and ATP, NADH, NADP, adrenaline, noradrenaline, and dopamine. Each of the ribonucleotides, the ribonucleosides, NADH, and NADP has a cis-diol structure, and hence are also compounds having a PBA binding site. As an example of a substance capable of competitive binding, ATP is described. That is, extracellularly, the bonds between the PBA groups of the polymer units α and the PBA binding sites of the polymer units β greatly contribute to the stabilization of the polymer micelle, whereas intracellularly (where ATP, which is a molecule capable of binding to the PBA group, is abundantly present), the bonds between the PBA groups and the PBA binding sites in the polymer micelle are replaced with bonds between the PBA groups and ATP. As a result, the bonds between the PBA groups and the PBA binding sites are cleaved, and hence the cross-linked structures dissociate and the polymer micelle can collapse. Substances capable of competitive binding preferably have a high PBA binding ability. For example, glucose, which is abundant in blood, has an ability to bind to the PBA group, but the binding ability is very low, and hence the bonds between the PBA groups and the PBA binding sites in the polymer micelle are maintained, and the polymer micelle is also stably maintained in blood.

Further, the cross-linked structure has the following effect: the cross-linked structure can be formed in a neutral environment with extreme ease. That is, a polymer micelle having formed therein the cross-linked structure can be easily formed by simply mixing the polymer unit α and the polymer unit β in a neutral aqueous medium. Therefore, a drug-encapsulating polymer micelle having excellent drug retention properties can be easily formed by simply mixing the polymer unit α, the polymer unit β, and the drug in a neutral aqueous medium. As specific examples, formation methods are mentioned that involve: mixing the polymer unit α and the polymer unit β in a neutral solvent, and then adding the drug, followed by further mixing; mixing the polymer unit α, the polymer unit β, and the drug in a neutral solvent; mixing the polymer unit α and the drug in a neutral solvent, and then adding the polymer unit β, followed by further mixing; or mixing the polymer unit β and the drug in a neutral solvent, and then adding the polymer unit α, followed by further mixing.

E. Drug

As the drug, any appropriate drug may be used as long as the drug can be encapsulated in the polymer micelle. An example of the drug that can be suitably encapsulated in the polymer micelle as described above is a nucleic acid. The nucleic acid is preferably a long-chain (that is, high-molecular-weight) nucleic acid, more preferably mRNA or pDNA. In the case of mRNA, binding to the PBA group at its 3' end is difficult, and as a result, binding to the polymer unit α is difficult. Accordingly, the encapsulation and retention by the polymer micelle having the cross-linked structure (s) are very useful. In the case of pDNA, binding to the PBA group is substantially impossible, and hence as in the case of the mRNA, the encapsulation and retention by the polymer micelle having the cross-linked structure(s) are very useful. Each nucleotide contained in the nucleic acid may be of a natural type or a chemically modified non-natural type, and may have added thereto an amino group, a thiol group, or a molecule such as fluorescent compound.

The content of the drug in the polymer micelle may be appropriately set according to the objectives and applications, etc. In case the drug is a nucleic acid, the N/P ratio is preferably from 1 to 100, more preferably from 1 to 50, still more preferably from 1 to 10. When the N/P ratio falls within such range, stability under physiological conditions is excellent and toxicity can be suppressed. The N/P ratio means [amino groups of polyamino acid side chains in polymer units contained in polymer micelle]/[phosphate groups in nucleic acid]

EXAMPLES

Hereinafter, although the present invention will be described concretely by way of Examples, the present invention is not limited to Examples below. It should be noted that in the Examples below, for example, the expression "PEG-PAsp(DET/FPBA$_{44}$)$_{75}$" means that its polyamino acid chain segment is one obtained by introducing 44 FPBA groups into a polyaspartic acid derivative having a polymerization degree (number of amino acid residues) of 75. In addition, the molecular weight of the PEG in each polymer unit synthesized in the Examples is 12,000.

Manufacturing Example 1: Synthesis of Polymer Unit α

(1-i) Synthesis of PEG-PBLA

PEG-PBLA (poly(β-benzyl-L-aspartic acid ester)) was synthesized in accordance with the following scheme.

[Chem. 12]

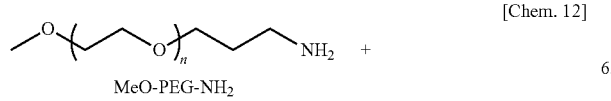

MeO-PEG-NH$_2$

+

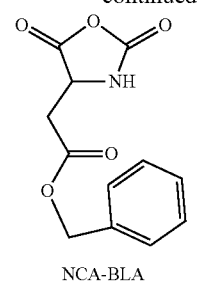

NCA-BLA

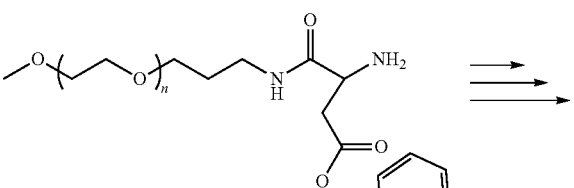

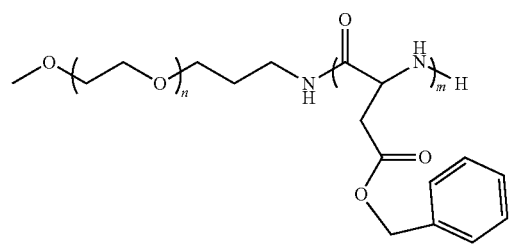

PEG-PBLA 505 mg of Methoxy(MeO)-PEG-NH$_2$ (manufactured by NOF Corporation, Mw=12,000) that had been lyophilized from benzene overnight was completely dissolved in 5.1 ml of a DMF:dichloromethane (1:10) mixed solvent. Under an Ar atmosphere, 920 mg of N-carboxy acid anhydride of β-benzyl-L-aspartic acid ester (BLA) (BLA-NCA, manufactured by Chuo Kaseihin Co., Inc.) was dissolved in 9.2 ml of the same mixed solvent as above. The BLA-NCA solution was added to the PEG solution, and the mixture was stirred in a water bath at 25° C. for 72 hours. After confirmation of the completion of the reaction by IR measurement, the reaction liquid was added dropwise to 300 ml of a stirred ethyl acetate:hexane (4:6) mixed solvent to provide a white precipitate of PEG-PBLA. The solvent was removed by suction filtration, followed by drying under reduced pressure. Thus, PEG-PBLA (1.11 g) was obtained as white powder. The polymerization degree (number of amino acid residues) of PBLA was 75.

(1-ii) Synthesis of PEG-PAsp(DET)

Next, PEG-PAsp(DET) was synthesized through an ester-amide exchange reaction between the PEG-PBLA and diethylenetriamine (DET). The synthesis scheme is as shown below.

[Chem. 13]

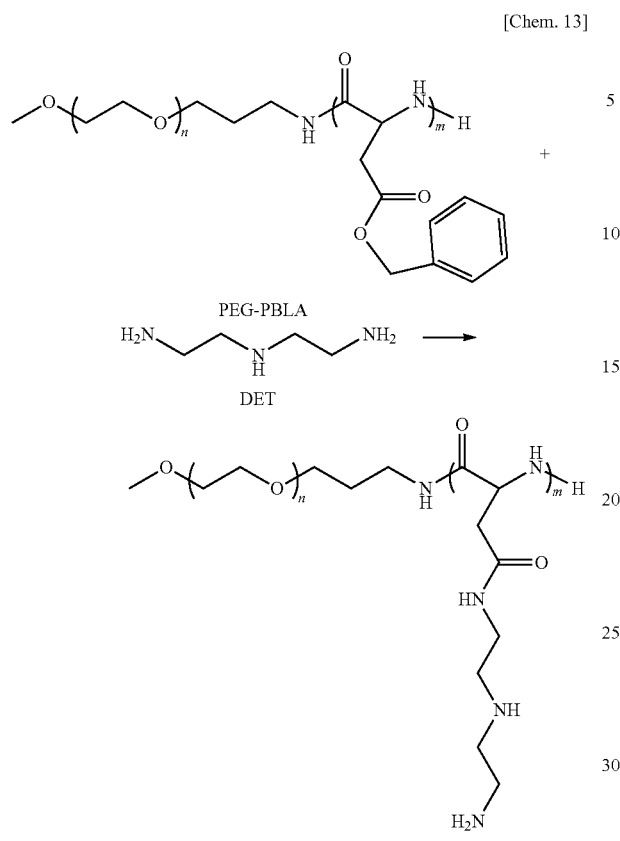

PEG-PBLA

DET

PEG-PAsp(DET)

[Chem. 14]

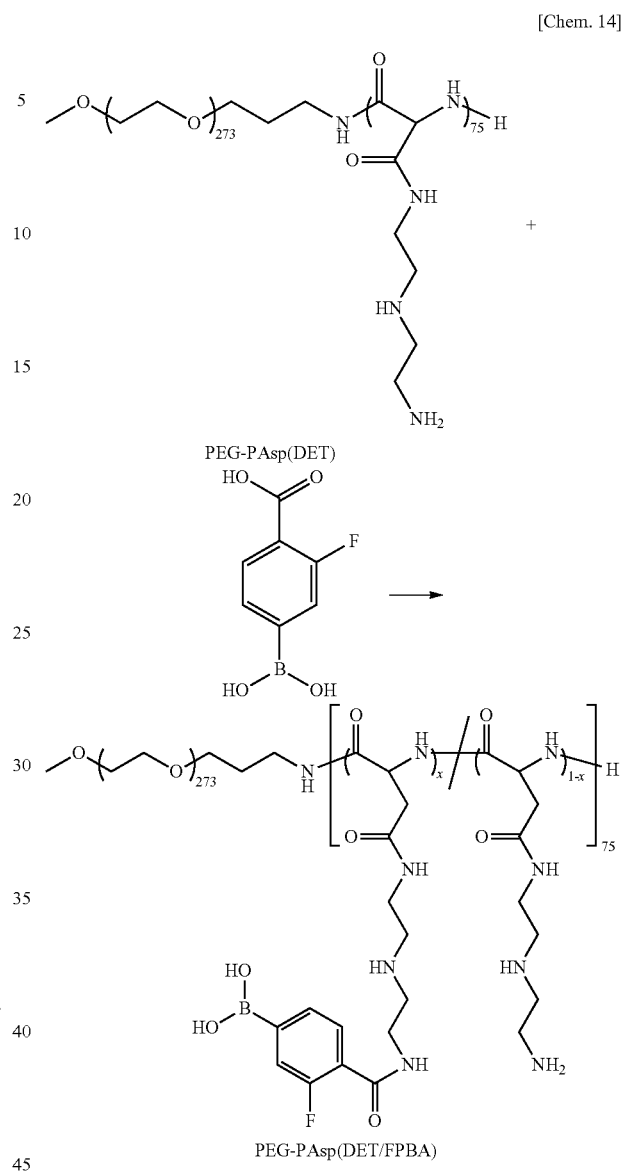

PEG-PAsp(DET)

PEG-PAsp(DET/FPBA)

600 mg of the PEG-PBLA was dissolved in a small amount of dichloromethane, and benzene was added, followed by lyophilization overnight. Under an Ar atmosphere, the lyophilized PEG-PBLA was dissolved in 30 ml of anhydrous N-methylpyrrolidone (NMP) containing 0.5 M thiourea. 50 Equivalents of anhydrous DET (9 ml) with respect to PBLA was taken in a separate flask, and dissolved in anhydrous NMP (9 ml). The PEG-PBLA solution and the DET solution were both cooled to 10° C., and the PEG-PBLA solution was slowly added dropwise to the DET solution. The mixture was allowed to react for about 2 hours. After the reaction, the reaction solution was added dropwise into a stirred 5 M aqueous solution of hydrochloric acid under cooling with salted ice. During the dropwise addition, the solution was prevented from exceeding 5° C. Immediately after the completion of the dropwise addition, dialysis was initiated at 4° C. with a 0.01 M aqueous solution of hydrochloric acid. The dialysis was performed three times with the 0.01 M aqueous solution of hydrochloric acid, and twice with pure water. After the dialysis, the resultant was lyophilized overnight, redissolved in a small amount of pure water, filtered with a 0.2 μm syringe filter, and lyophilized again overnight. Thus, PEG-PAsp(DET) (551 mg) was obtained.

(1-iii) Introduction of PBA Groups into PEG-PAsp(DET)

Next, PBA groups (in this Manufacturing Example, FPBA groups) were introduced into side chains of PEG-PAsp(DET) through a dehydration condensation reaction using a triazine-based condensing agent DMT-MM. The reaction scheme is as shown below.

40 mg of PEG-PAsp(DET), 155 mg of DMT-MM (manufactured by Wako Pure Chemical Industries, Ltd.), and 102 mg of mannitol were dissolved in 7.5 ml of a 20 mM $NaHCO_3$ solution. Meanwhile, FPBA (manufactured by Wako Pure Chemical Industries, Ltd.) in an amount corresponding to a predetermined introduction ratio as shown in Table 1 below was dissolved in methanol. The FPBA was dissolved in 2 ml of methanol when having a mass of 10 mg or less, and the FPBA was dissolved in 7.5 ml of methanol when having a mass of more than 10 mg. The PEG-PAsp (DET) and the FPBA solution were mixed, and while 155 mg of DMT-MM (manufactured by Wako Pure Chemical Industries, Ltd.) was added every 1 hour, the mixture was allowed to react while being stirred at 4° C. for 3 hours. Immediately after the reaction, dialysis was initiated at 4° C. with a 0.01 M aqueous solution of hydrochloric acid. The dialysis was performed three times with the 0.01 M aqueous solution of hydrochloric acid, and twice with pure water. After the dialysis, the resultant was filtered with a 0.2 μm syringe filter and lyophilized to provide PEG-PAsp(DET/

FPBA). Analysis by 1H-NMR found that the actual introduction numbers of FPBA groups were as shown in Table 1.

TABLE 1

| Manufacturing Example | 1A | 1B | 1C | 1D | 1E | 1F |
|---|---|---|---|---|---|---|
| Amount of FPBA (mg) | 4.2 | 8.3 | 12.6 | 14.7 | 16.8 | 25.2 |
| Theoretical introduction number | 15 | 30 | 45 | 56 | 68 | 75 |
| Actual introduction number | 11 | 19 | 44 | 56 | 67 | 71 |

Production Example 2: Synthesis of Polymer Unit β

(2-i) Synthesis of PEG-PAsp(DET)

PEG-PAsp(DET) was synthesized in the same manner as in Manufacturing Example 1.

(2-ii) Synthesis of Gluconic Acid Derivative (Polyol)

A gluconic acid derivative (polyol) was synthesized by allowing gluconolactone to react with γ-aminobutyric acid to open its ring. The synthesis scheme is as shown below.

[Chem. 15]

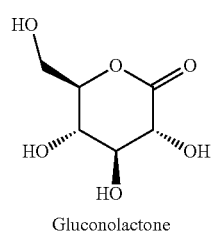
Gluconolactone

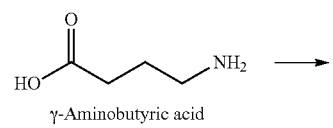
γ-Aminobutyric acid

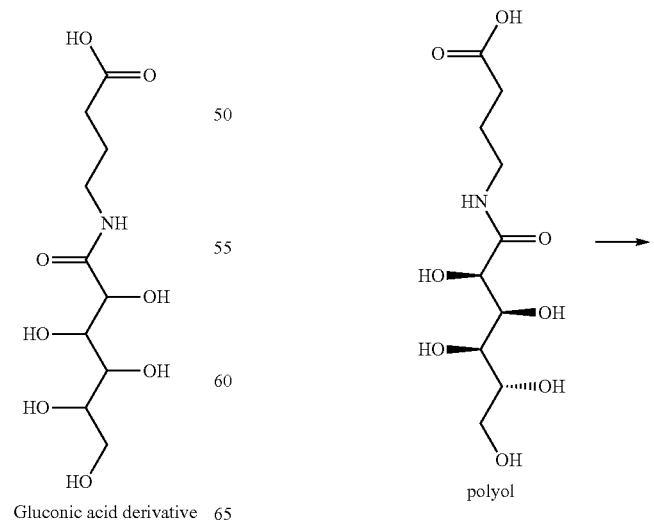
Gluconic acid derivative 89 mg of gluconolactone (0.5 mmol, manufactured by Tokyo Chemical Industry Co., Ltd.) and 52 mg of γ-aminobutyric acid (0.5 mmol, manufactured by Tokyo Chemical Industry Co., Ltd.) were mixed, and the mixture was dissolved in a mixed solvent of 14 ml of methanol and 1.5 ml of triethylamine. The solution was subjected to reaction by being left to stand overnight while being refluxed at 75° C. After the completion of the reaction, the resultant was recrystallized from an ethyl acetate:hexane (1:1) mixed solvent, and dried under reduced pressure to provide a gluconic acid derivative.

(2-iii) Introduction of Polyol Structure into PEG-PAsp (DET)

Next, polyol structures were introduced into side chains of PEG-PAsp(DET) through a dehydration condensation reaction using a triazine-based condensing agent DMT-MM between PEG-PAsp(DET) and the gluconic acid derivative. A reaction scheme is as shown below.

[Chem. 16]

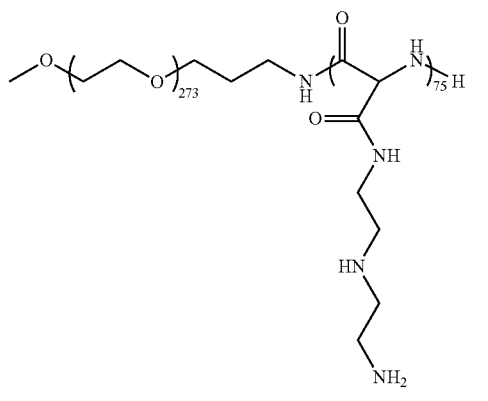
PEG-PAsp(DET)

+ polyol

-continued

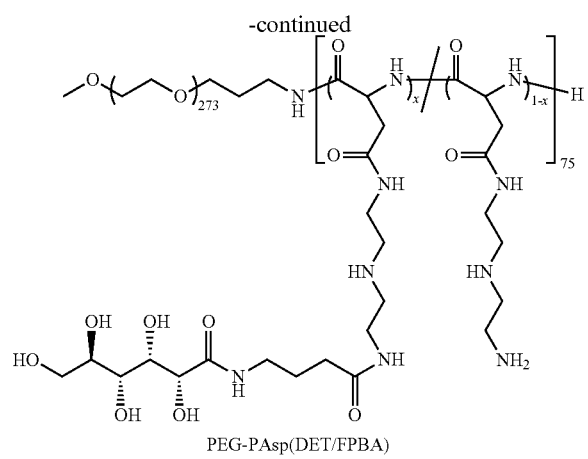

PEG-PAsp(DET/FPBA)

40 mg of PEG-PAsp(DET), 155 mg of DMT-MM (manufactured by Wako Pure Chemical Industries, Ltd.), and the gluconic acid derivative in an amount corresponding to a predetermined introduction ratio as shown in Table 2 below were dissolved in a 10 mM NaHCO$_3$ solution. The system for the intended introduction number of 75 was frozen at −20° C. and thawed to perform the reaction (freeze-thaw method). In each of the other three systems, the reaction was performed under stirring at 4° C. for 3 hours. Immediately after the reaction, dialysis was initiated at 4° C. with a 0.01 M aqueous solution of hydrochloric acid. The dialysis was performed three times with the 0.01 M aqueous solution of hydrochloric acid, and twice with pure water. After the dialysis, the resultant was filtered with a 0.2 μm syringe filter and lyophilized to provide PEG-PAsp(DET/polyol). Analysis by 1H-NMR found that the actual introduction numbers of polyol structures were as shown in Table 2.

TABLE 2

|  | Manufacturing Example | | | |
| --- | --- | --- | --- | --- |
|  | 2A | 2B | 2C | 2D |
| Amount of gluconic acid derivative (mg) | 5.3 | 7.9 | 10.5 | 26.5 |
| Theoretical introduction number | 15 | 22 | 30 | 75 |
| Actual introduction number | 7 | 11 | 20 | 40 |

Example A: Preparation of pDNA-Encapsulating Polymer Micelle

The polymer units α obtained in Manufacturing Examples 1A to 1F above and the polymer units β obtained in Manufacturing Examples 2A to 2D above were used in combination to prepare polymer micelle solutions. Specifically, the polymer micelle solutions were each prepared by the following procedure. The polymer units α and the polymer units β were each dissolved in a 10 mM HEPES solution (pH 7.4) at 1 mg/ml. The concentrations of those solutions were adjusted corresponding to an N/P ratio. 5 μl of a solution of polymer unit α and 5 μl of a solution of polymer unit β were mixed, and then 20 μl of 50 μg/ml (1 OD) of pDNA was added to prepare a solution of a pDNA-encapsulating polymer micelle. In the following evaluations, the solutions of pDNA-encapsulating polymer micelles were prepared using pCAG-Luc2 as the pDNA only in the blood retentivity evaluation, and using pCAG-Luc as the pDNA in other evaluations. Specifically, pCAG-Luc means an expression vector obtained by incorporating a Luciferase gene (SEQ ID NO: 1) downstream of the CAG promoter of a pCAGGS vector (Niwa et al., Gene 108, 193-200, 1991). pCAG-Luc2 means an expression vector obtained by incorporating a Luciferase gene (SEQ ID NO: 3) downstream of the CAG promoter of a pCAGGS vector (Niwa et al., Gene 108, 193-200, 1991).

Comparative Example 1

A solution of a pDNA-encapsulating polymer micelle was prepared in the same manner as in the Example except that the polymer unit α (50%) and PEG-PAsp(DET) (50%) synthesized in Manufacturing Example 1 were used.

Comparative Example 2

A solution of a pDNA-encapsulating polymer micelle was prepared in the same manner as in the Example except that the polymer unit β (50%) synthesized in Manufacturing Example 2 and PEG-PAsp(DET) (50%) synthesized in Manufacturing Example 1 were used.

Comparative Example 3

A solution of a pDNA-encapsulating polymer micelle was prepared in the same manner as in the Example except that only PEG-PAsp(DET) synthesized in Manufacturing Example 1 was used.

<Particle Diameter of Polymer Micelles>

Polymer micelles were prepared for all combinations of the polymer units α obtained in Manufacturing Examples 1A to 1F above and the polymer units β obtained in Manufacturing Examples 2A to 2D above. The resultant polymer micelle solutions were left to stand at 4° C. overnight, and then subjected to DLS measurement with a Zetasizer Nano-ZS (Malvern) to measure the particle diameters of the polymer micelles. As a result, the formation of polymer micelles was confirmed for each of the combinations. For example, the polymer micelle of the combination of the polymer unit α [PEG-PAsp(DET/FPBA$_{44}$)$_{75}$] of Manufacturing Example 1C and the polymer unit β [PEG-PAsp(DET/polyol$_{20}$)$_{75}$] of Manufacturing Example 2C had an average particle diameter of 103.2 nm and a polydispersity of 0.172.

<Polyanion Resistance Test>

Figure 1B:
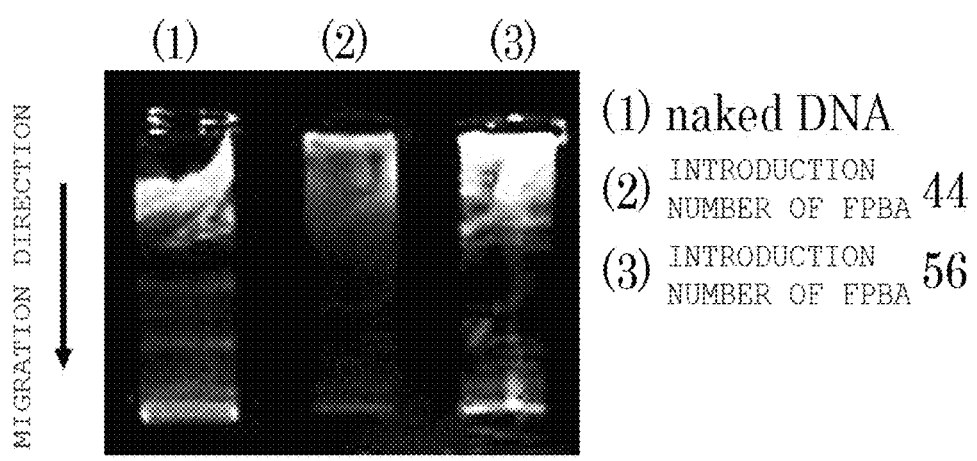
FIG. 1B is an electrophoresis result that compares and shows replacement resistances of a polymer micelle to polyanion for A/P=8 in cases in which the introduction number of polyol structures was fixed at 40 while the introduction number of FPBA groups was varied.

First, Using Combinations of the Polymer Unit β [PEG-PAsp(DET/polyol$_{40}$)$_{75}$] of Manufacturing Example 2D with the polymer units α of Manufacturing Examples 1A to 1F, replacement resistances to polyanion were compared in cases in which the introduction number of polyol structures was fixed at 40 while the introduction number of FPBA groups was varied. The procedure is as described below. A 1×TAE weak buffer was prepared so as to contain Tris at 3.3 mM, sodium acetate at 1.7 mM, and EDTA-2Na at 1 mM, and was used as an electrophoresis buffer. The TAE buffer was added to 0.54 g of agarose to a total amount of 60 g, 15 g of pure water was added, and then the resultant was heated in a microwave oven and cooled to produce 0.9 wt % agarose gel. To each polymer micelle solution having its N/P ratio adjusted to 3, 10 μl of dextran sulfate corresponding to an A/P ratio (molar ratio of anionic charges to phosphate groups of pDNA) and 10 μl of a 750 mM NaCl solution were added, and then the mixtures were incubated at 37° C. for 1 hour. After the incubation, a loading buffer was added and electrophoresis was performed at 100 V for 60 minutes to confirm the presence or absence of the release of pDNA. The results for A/P=6 and A/P=8 are shown in FIG. 1A and FIG. 1B, respectively. It is found from FIG. 1A and FIG. 1B that when the introduction number of polyol structures is fixed to 40, the polymer micelle having an introduction number of FPBA groups of 44 shows the highest stability (replacement resistance to polyanion).

Figure 1C:
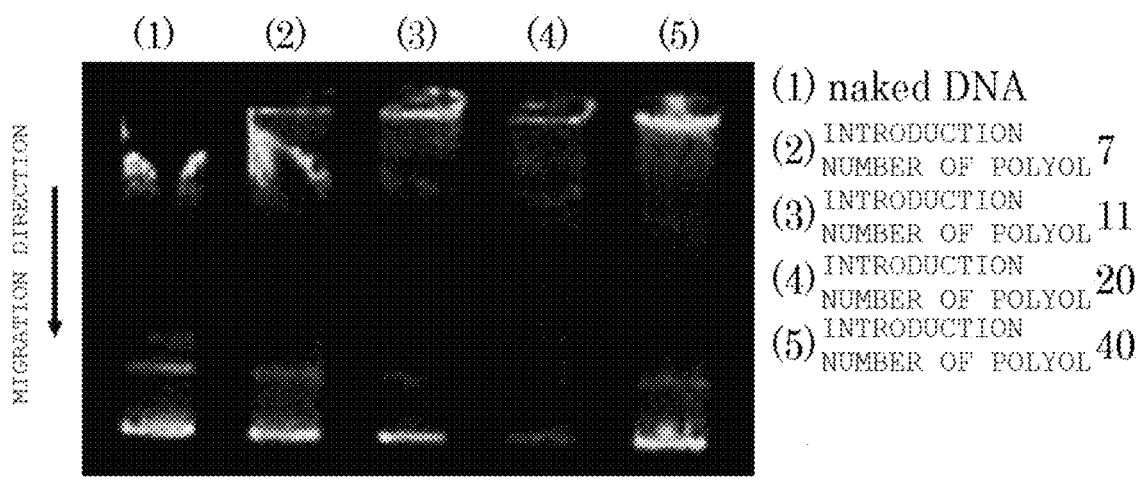
FIG. 1C is an electrophoresis result that compares and shows replacement resistances of a polymer micelle to polyanion in cases in which the introduction number of FPBA groups was fixed at 44 while the introduction number of polyol structures was varied.

In view of the above-mentioned results, replacement resistances to polyanion were compared in cases in which the introduction number of FPBA groups was fixed at 44 while the introduction number of polyol structures was varied. That is, the polymer unit α [PEG-PAsp(DET/FPBA$_{44}$)$_{75}$] of Manufacturing Example 1C and the polymer units β of Manufacturing Examples 2A to 2D were used in combination. The procedure is the same as above. The result is shown in FIG. 1C. It is found from FIG. 1C that the polymer micelle obtained from the polymer unit α [PEG-PAsp(DET/FPBA$_{44}$)$_{75}$] of Manufacturing Example 1C and the polymer unit β [PEG-PAsp(DET/polyol$_{20}$)$_{75}$] of Manufacturing Example 2C exhibits the highest stability (replacement resistance to polyanion). Therefore, it is suggested that such a polymer micelle does not easily collapse owing to, for example, electrostatic interactions with anionic molecules abundantly present in vivo, etc., and hence excels in stability and drug retention properties in vivo.

<ATP Concentration Responsiveness>

Figure 2:
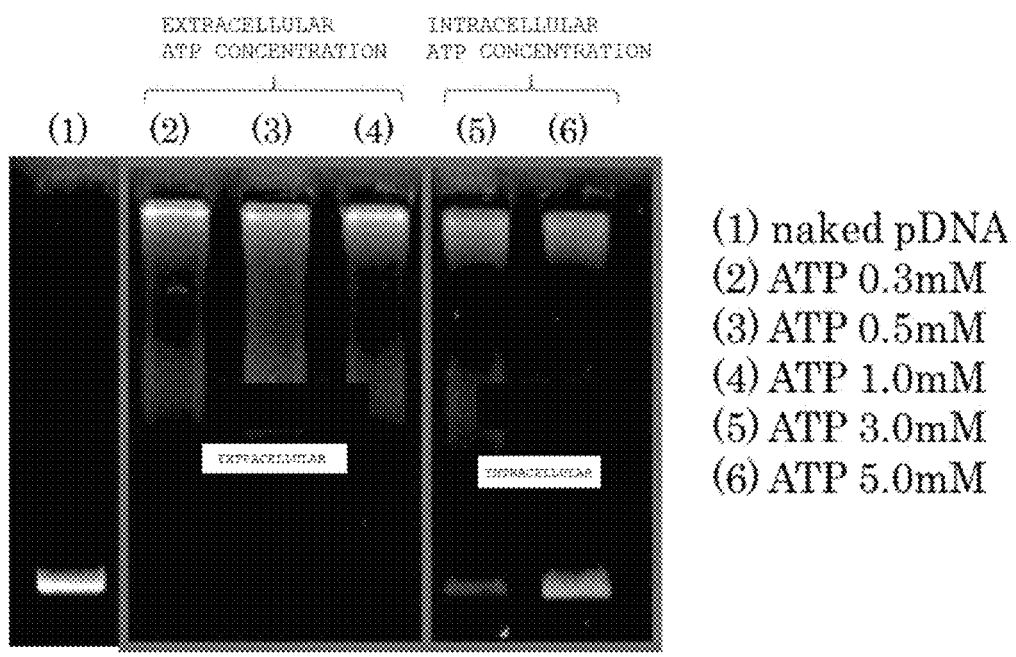
FIG. 2 is an electrophoresis result that shows the ATP concentration responsiveness of a polymer micelle of an Example.

The polymer micelle obtained from the polymer unit α [PEG-PAsp(DET/FPBA$_{44}$)$_{75}$] of Manufacturing Example 1C and the polymer unit β [PEG-PAsp(DET/polyol$_{20}$)$_{75}$] of Manufacturing Example 2C, which exhibited the highest stability in the "Polyanion Resistance Test", was used (but, the N/P ratio was set to 3.5). Agarose gel was produced in the same manner as in the "Polyanion Resistance Test". 5 μl of ATP solutions prepared to have concentrations of 0.3 mM, 0.5 mM, 1.0 mM, 3.0 mM, or 5.0 mM after mixing and 5 μl of a 750 mM NaCl solution were added to 15 μl of the polymer micelle solution, and the mixtures were incubated at 37° C. for 2 hours. After the incubation, electrophoresis was performed at 100 V for 60 minutes to confirm the presence or absence of the release of pDNA. The result is shown in FIG. 2. It is found from FIG. 2 that pDNA is not released at an ATP concentration of from 0.3 mM to 1.0 mM, and pDNA is released at an ATP concentration of 3.0 mM or more. Because extracellular ATP concentration is about 0.3 mM and intracellular ATP concentration is about 3 mM, it is suggested that the polymer micelle has responsiveness to the intracellular ATP concentration.

<Glucose Resistance>

Figure 3:
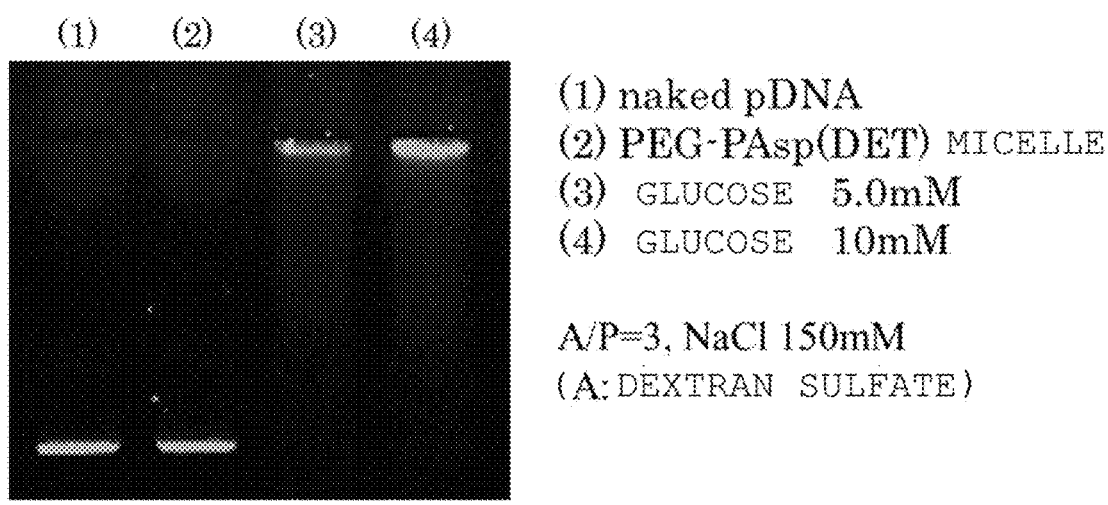
FIG. 3 is an electrophoresis result that shows the glucose resistance of the polymer micelle of an Example.

The same polymer micelle as that in the "ATP Concentration Responsiveness" was used, and the same agarose gel as that in the "ATP Concentration Responsiveness" was produced. 5 μl of glucose solutions prepared with dextran sulfate of A/P ratio=3 so as to have concentrations of 5.0 mM or 10 mM after mixing and 5 μl of a 750 mM NaCl solution were added to 15 μl of the polymer micelle solution, and the mixtures were incubated at 37° C. for 1 hour. After the incubation, electrophoresis was performed at 100 V for 60 minutes to confirm the presence or absence of the release of pDNA. The result is shown in FIG. 3. Because the blood glucose concentration is about 5.6 mM in a healthy subject and is about 10 mM in a diabetic patient, it is suggested from FIG. 3 that the collapse of the polymer micelle due to a replacement reaction between the gluconic acid derivative moiety (polyol structure) in the polymer micelle and glucose does not occur.

<Cellular Uptake Evaluation>

Human hepatoma cells (Huh-7) were seeded into a 6-well plate at 50,000 cells/i ml/well and cultured at 37° C. for 24 hours. After exchanging with fresh medium, a polymer micelle prepared using pDNA labeled with Cy-5 so as to have a pDNA concentration of 2/3 OD corresponding to the N/P ratio was added at 75 μl/well, followed by culture at 37° C. for 24 hours. After the culture, the medium was removed, cell surfaces were washed three times with D-PBS(–), and a 10-fold diluted Trypsin-EDTA solution was added at 1 ml/well and allowed to spread over the entire well, followed by the removal of the Trypsin-EDTA solution and incubation at 37° C. for 3 minutes. D-PBS(–) was added at 1 ml/well to detach the cells, and the resultant cell suspension was evaluated with a flow cytometer. The polymer unit α [PEG-PAsp(DET/FPBA$_{44}$)$_{75}$] of Manufacturing Example 1C and the polymer unit β [PEG-PAsp(DET/polyol$_{20}$)$_{75}$] of Manufacturing Example 2C were used as the polymer units for forming the polymer micelle. In the following in vitro and in vivo evaluations, the polymer micelle formed of the polymer unit α [PEG-PAsp(DET/FPBA$_{44}$)$_{75}$] of Manufacturing Example 1C and the polymer unit β [PEG-PAsp(DET/polyol$_{20}$)$_{75}$] of Manufacturing Example 2C is defined as the Example. As described above, a polymer micelle formed of 50% of the corresponding polymer unit α and 50% of PEG-PAsp(DET) was used as Comparative Example 1, a polymer micelle formed of 50% of the corresponding polymer unit β and 50% of PEG-PAsp(DET) was used as Comparative Example 2, and a polymer micelle formed only of PEG-PAsp(DET) was used as Comparative Example 3.

Figure 4:
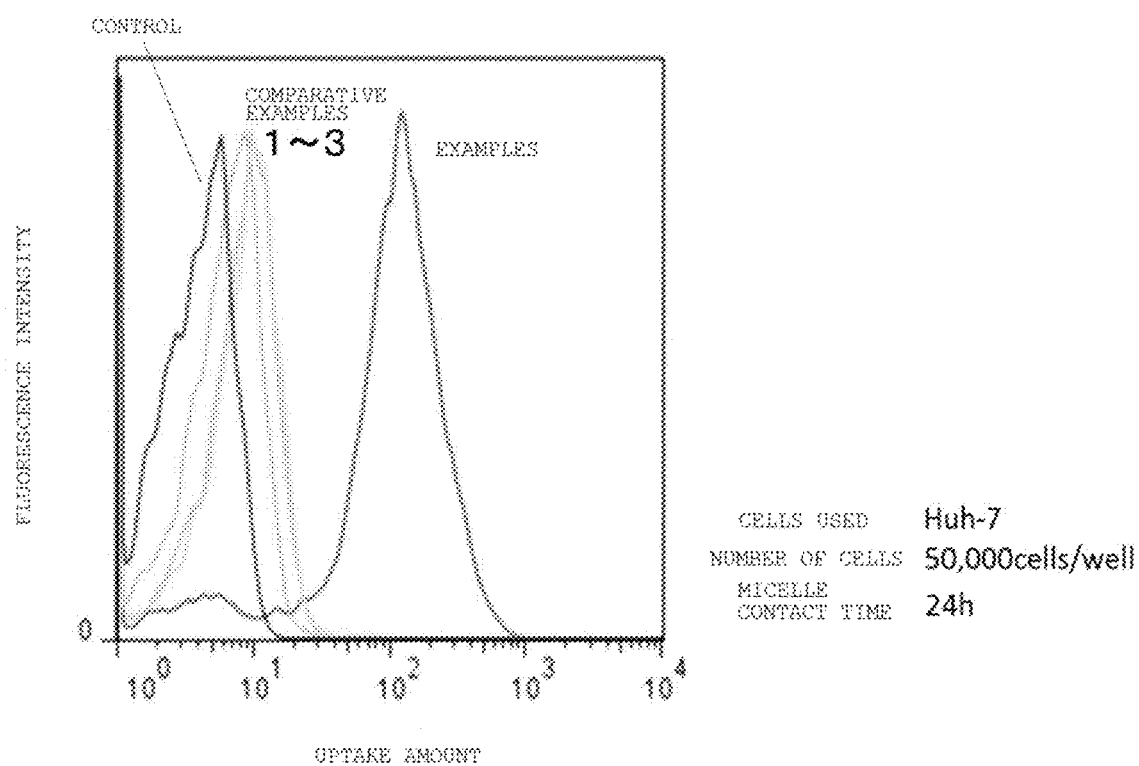
FIG. 4 is a graph that compares and shows cellular uptake evaluations for the polymer micelle of an Example and polymer micelles of Comparative Examples 1 to 3.

The results of this evaluation are shown in FIG. 4. From FIG. 4, high cellular uptake was observed only in the case of the polymer micelle of the Example. Specifically, the polymer micelle of the Example showed an uptake amount about 10 times as large as those of the polymer micelles of Comparative Examples 1 to 3. This is presumably due to the stabilization of the polymer micelle of the Example by virtue of its internal cross-linked structure (cross-linked structures between the PBA groups and the polyol structures) unlike the polymer micelles of Comparative Examples 1 to 3.

<Gene Expression Test by Luciferase Assay>

Huh-7 cells were seeded into a 24-well plate at 20,000 cells/400 μl/well and cultured at 37° C. for 24 hours. After exchange with fresh medium, a polymer micelle prepared using pCAG-Luc so as to have a pCAG-Luc concentration of 2/3 OD corresponding to the N/P ratio was added at 30 μl/well, followed by culture at 37° C. for 24 hours. After that, the medium was exchanged with a fresh one, followed again by culturing at 37° C. for 24 hours. After that, the medium was removed, cell surfaces were washed a few times with D-PBS(–), and 5-fold diluted Cell Culture Lysis Buffer was added at 200 μl/well, followed by incubation at room temperature for 1 hour. After the incubation, the resultant cell lysate was added to a 96-well plate at 20 μl/well, Luciferase Assay System Kit was added at 100 μl/well, and then the luciferase luminescence amount was evaluated with a luminometer.

In parallel, a cytotoxicity test was performed for each of the polymer unit α [PEG-PAsp(DET/FPBA$_{44}$)$_{75}$], the polymer unit β [PEG-PAsp(DET/polyol$_{20}$)$_{75}$], and PEG-PAsp (DET). Specifically, the cytotoxicity test was performed as described below. Huh-7 cells were seeded into a 96-well plate at 5,000 cells/100 μl/well and cultured at 37° C. for 24 hours, and then the polymers dissolved in a 10 mM HEPES solution (pH 7.4) were added, followed by culturing at 37° C. for 48 hours. After that, Cell Counting Kit was added at 10 µl/well, followed by culturing at 37° C. for 1.5 hours and measurement of absorbance at 450 nm.

Figure 5:
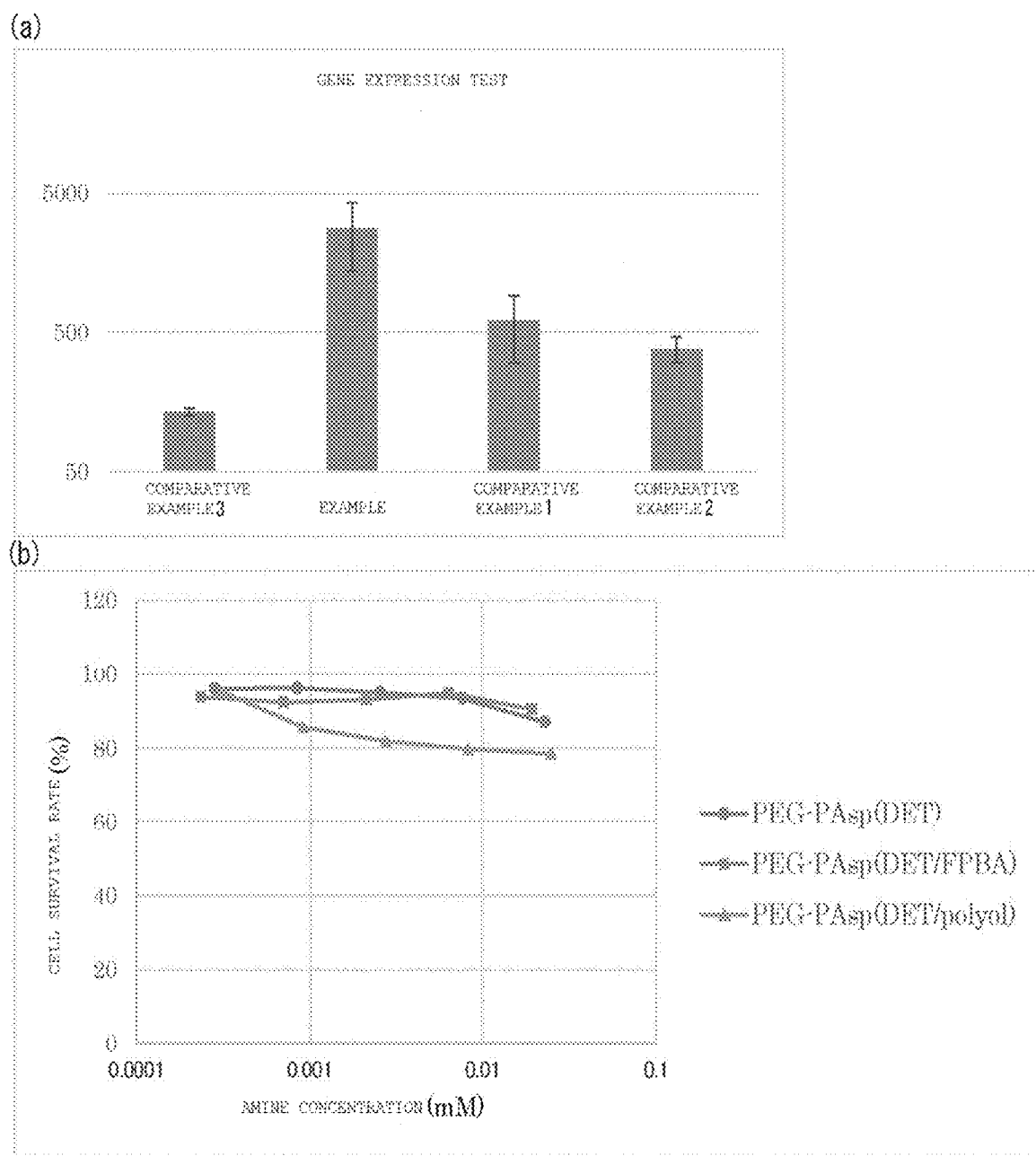
FIG. 5($a$) is a graph that shows gene expression evaluations for the polymer micelle of an Example and the polymer micelles of Comparative Examples 1 to 3, and FIG. 5($b$) is a graph that shows cytotoxicity evaluations of polymers constituting the polymer micelles.

The cytotoxicity evaluations of the polymers and the gene expression evaluation of the polymer micelles are shown in FIG. 5. As is apparent from FIG. 5(b), none of the polymer units constituting the polymer micelles is found to have remarkable cytotoxicity, suggesting that the polymer micelles do not have cytotoxicity. As is apparent from FIG. 5(a), in the gene expression test, the polymer micelle of the Example exhibited an expression efficiency that was about 8 or more times as high as that of the polymer micelles of any of Comparative Examples 1 to 3, and that was about 20 times as high as that of the polymer micelle of Comparative Example 3. This indicates that the polymer micelle that was taken up actually released pDNA in cells. In addition, the difference in the cellular uptake amount described above is about 10 times between the Example and the Comparative Examples, whereas about 20-fold expression efficiency is shown. This indicates that there is a difference during the period from the intracellular uptake of the polymer micelle to the expression, suggesting the possibility that the polymer micelle of the Example responds to the intracellular ATP concentration.

<Blood Retentivity Evaluation>

200 µl of a polymer micelle solution prepared so as to have a pDNA concentration of 2.0 OD was administered to mice through the tail veins (N=4). After 5 minutes, 10 minutes, 20 minutes, and 40 minutes, 2 µl of blood was collected from the tail veins, and mixed with a mixed solution formed of PBS/EDTA/Proteinase K. In addition, a micelle solution having its pDNA concentration set to 1/5 OD was mixed with the mixed solution, and the resultant was used as a control value at 0 minutes. pDNA was extracted from the collected blood sample using DNeasy Blood & Tissue Kit. 2 µl of the extracted pDNA solution was mixed with 18 µl of a solution formed of SYBR Green, primers, and ultrapure water, and PCR measurement was performed.

Figure 6:
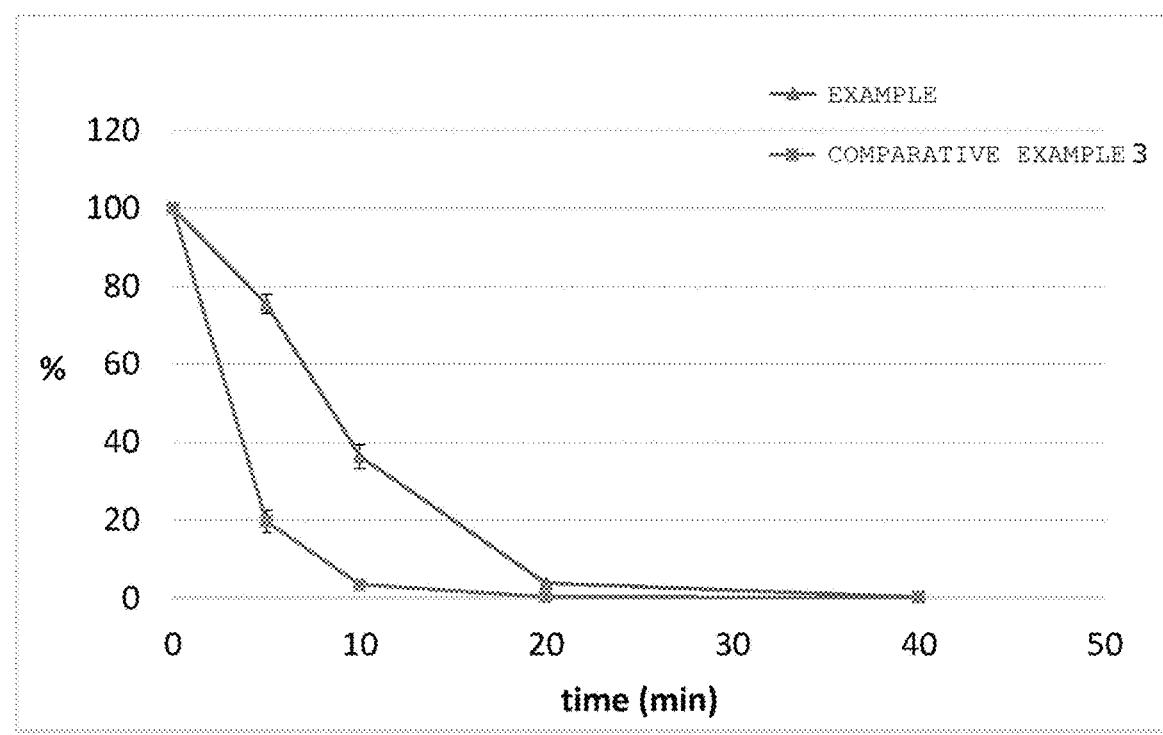
FIG. 6 is a graph that shows blood retentivity evaluations for the polymer micelle of an Example and the polymer micelle of Comparative Example 3.

The results of this evaluation are shown in FIG. 6. As apparent from FIG. 6, the polymer micelle of the Example is found to be significantly improved in blood retentivity as compared to the polymer micelle of Comparative Example 3. That is, it was found that the polymer micelle of the Example had excellent stability even in an in vivo environment. This indicates that the effect of the cross-linking between the PBA groups and the polyol structures is useful even in an in vivo environment.

Example B: Preparation of mRNA-Encapsulating Polymer Micelle

The polymer unit α [PEG-PAsp(DET/FPBA$_{44}$)$_{75}$] of Manufacturing Example 1C and the polymer unit β [PEG-PAsp(DET/polyol$_{20}$)$_{75}$] of Manufacturing Example 2C were used in combination to prepare a polymer micelle solution. Specifically, the polymer micelle solution was prepared by the following procedure. The polymer unit α and the polymer unit β were each dissolved in a 10 mM HEPES solution (pH 7.4) at 1 mg/ml. The concentrations of those solutions were adjusted correspondingly to the N/P ratio. 5 µl of the solution of the polymer unit α and 5 µl of the solution of the polymer unit β were mixed, and then 0.25 µg of luciferase-encoding mRNA was added to prepare a solution of a mRNA-encapsulating polymer micelle of the Example (N/P ratio=3, mRNA concentration=2/3 OD). In addition, a solution of a mRNA-encapsulating polymer micelle of the Comparative Example was prepared in the same manner except that [PEG-PAsp(DET)$_{75}$] was used as the polymer unit α. The luciferase-encoding mRNA was prepared using pCAG-Luc2 as the template and using an RNA synthesis kit (manufactured by Life Technologies Japan Ltd., product name: "mMESSAGE mMACHINE@Kit").

<Gene Expression Test by Luciferase Assay>

Huh-7 cells were seeded into a 48-well plate at 10,000 cells/200 µl/well and cultured at 37° C. for 24 hours. After exchanging with fresh medium, the polymer micelle of the Example or the Comparative Example was added at 15 µl/well, followed by culturing at 37° C. for 24 hours. After that, the medium was removed, cell surfaces were washed a few times with D-PBS(-), and 5-fold diluted Cell Culture Lysis Buffer was added at 200 µl/well, followed by incubation at room temperature for 1 hour. After the incubation, the resultant cell lysate was added to a 96-well plate at 20 µl/well, Luciferase Assay System Kit was added at 100 µl/well, and then the luciferase luminescence amount was evaluated with a luminometer (N=4). The results are shown in FIG. 7.

Figure 7:
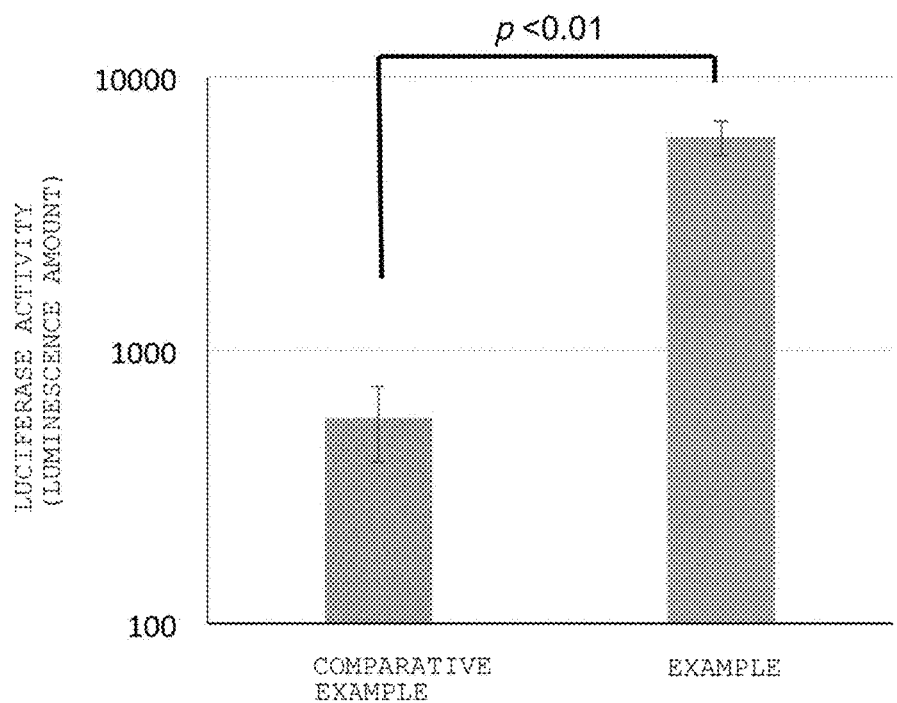
FIG. 7 is a graph that shows gene expression evaluations for the polymer micelle of an Example and the polymer micelle of a Comparative Example.

As apparent from FIG. 7, in the gene expression test, the polymer micelle of the Example exhibited an expression efficiency about 10 times as high as that of the polymer micelle of the Comparative Example. This indicates the polymer micelle that was taken up actually released mRNA in cells.

The pharmaceutical composition of the present invention can be suitably applied in the field of DDS.

The invention claimed is:

1. A pharmaceutical composition, comprising a micelle formed by block copolymers α and β, each having formula (1) or (2), wherein the block copolymer α and the block copolymer β are radially arranged in the micelle such that cationic polymer chain segments are directed inward and hydrophilic polymer chain segments are directed outward, and a nucleic acid encapsulated within the micelle, wherein the formulas (1) and (2) are as follows:

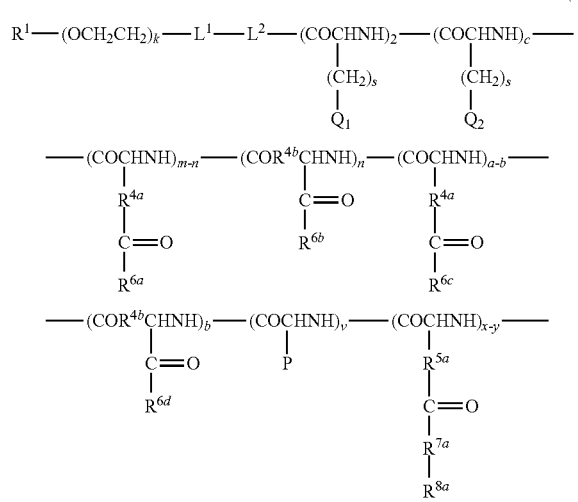

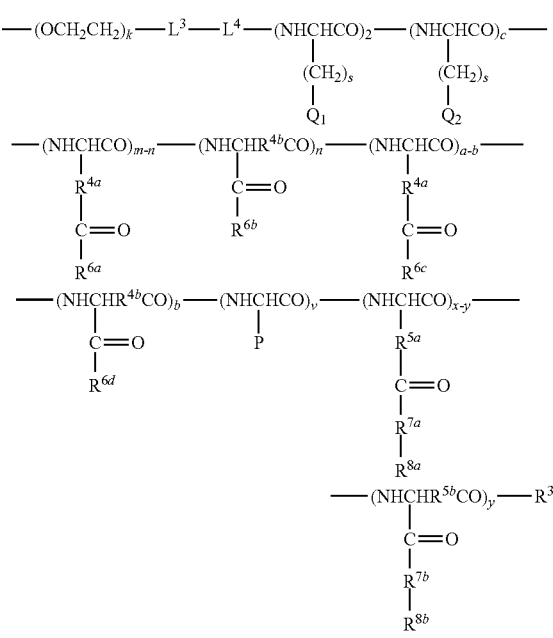

wherein:
R¹ is a hydrogen atom, an unsubstituted or substituted, linear or branched, alkyl group having 1 to 12 carbon atoms or a group containing a target binding site;
R² is a hydrogen atom, an unsubstituted or substituted, linear or branched, alkyl group having 1 to 12 carbon atoms, or an unsubstituted or substituted, linear or branched, alkylcarbonyl group having 1 to 24 carbon atoms;
R³ is a hydroxyl group, an unsubstituted or substituted, linear or branched, alkyloxy group having 1 to 12 carbon atoms, an unsubstituted or substituted, linear or branched, alkenyloxy group having 2 to 12 carbon atoms, an unsubstituted or substituted, linear or branched, alkynyloxy group having 2 to 12 carbon atoms, or an unsubstituted or substituted, linear or branched, alkyl-substituted imino group having 1 to 12 carbon atoms;
$R^{4a}$, $R^{4b}$, $R^{5a}$, and $R^{5b}$ are each independently a methylene group or an ethylene group;
$R^{6a}$ and $R^b$ are each independently a group selected from the following formulas (i) to (iv):

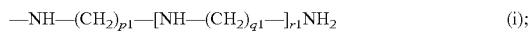  (i);

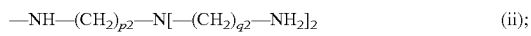  (ii);

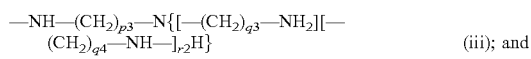  (iii); and

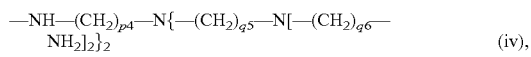  (iv), wherein p1 to p4, q1 to q6, and r1 and r2 each are independently an integer of from 1 to 5;
$R^{6c}$ and $R^{6d}$ are each independently a group obtained by introducing a saturated or unsaturated, linear or branched, aliphatic hydrocarbon group having 6 to 27 carbon atoms, an aromatic hydrocarbon group having 6 to 27 carbon atoms, or a steryl group into an amino group of a group selected from the above formulas (i) to (iv);
$R^{7a}$ and $R^{7b}$ are each independently —O— or —NH—;
$R^{8a}$ and $R^{8b}$ are each independently a saturated or unsaturated, linear or branched, aliphatic hydrocarbon group having 6 to 27 carbon atoms, an aromatic hydrocarbon group having 6 to 27 carbon atoms, or a steryl group;
$Q_1$ is —NH₂, —NHC(=NH)NH₂, or a group having the following formula (II):

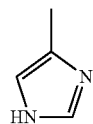  (II)

$Q_2$ is a group, in which a saturated or unsaturated, linear or branched, aliphatic hydrocarbon group having 6 to 27 carbon atoms, an aromatic hydrocarbon group having 6 to 27 carbon atoms, or a steryl group is introduced into an (the) amino group of —NH₂, —NHC(=NH) NH₂, or the group represented by said formula (II);
P is a side chain of leucine, isoleucine, phenylalanine, methionine, or tryptophan;
$L^1$ and $L^3$ are each independently —S—S— or a valence bond;

$L^2$ is —NH—, —O—, —O(CH₂)$_{p1}$—NH—, or -$L^{2a}$-(CH₂)$_{q1}$-$L^{2b}$-, where p1 and q1 are each independently an integer of from 1 to 5, $L^{2a}$ is OCO, OCONH, NHCO, NHCOO, NHCONH, CONH, or COO, and $L^{2b}$ is NH or O;
$L^4$ is —OCO—(CH₂)$_{p2}$—CO—, —NHCO—(CH₂)$_{p3}$—CO—, or -$L^{4a}$-(CH₂)$_{q2}$—CO—, where p2, p3, and q2 are each independently an integer of from 1 to 5, and $L^{4a}$ is OCONH, —CH₂NHCO—, NHCOO, NHCONH, CONH, or COO;
k is an integer of from 30 to 20,000;
s is an integer of from 1 to 6;
m is an integer of from 0 to 300;
n is an integer of from 0 to m;
a is an integer of from 0 to 300;
b is an integer of from 0 to a;
v is an integer of from 0 to 300;
c is an integer of from 0 to 300;
x is an integer of from 0 to 300;
y is an integer of from 0 to x;
z is an integer of from 0 to 300;
with the proviso that,
when m is 0, z is an integer of 2 or more;
when z is 0, m is an integer of 1 or more; and
when the sum of a total number of primary amino groups and secondary amino groups contained in (COCHNH)$_Z$ or (NHCHCO)$_Z$ and a total number of primary amino groups and secondary amino groups contained in (m-n) of $R^{6a}$ and n of $R^{6b}$, is defined as w, j hydrogen atom(s) of the amino group(s) is (are) each substituted with an organic group having a substituted phenylboronic acid (PBA) group in block copolymer α, and h hydrogen atom(s) of the amino group(s) is (are) each substituted with an organic group having a PBA binding site in block copolymer β, where j and h are each independently 1 or more but less than w;
PBA groups of block copolymer α are cross-linked to PBA binding sites of block copolymer β;
the PBA binding sites each contain a polyol having a cis-diol structure;
the binding order of the amino acid residue(s) having the cationic side chain(s), the amino acid residue(s) containing the substituted PBA group(s), and the amino acid residue(s) containing the hydrophobic side chain (s) and the amino acid residue(s) containing the PBA binding site(s) is arbitrary;
the nucleic acid is selected from the group consisting of pDNA or mRNA; and
the substituted PBA group has the following formula (I):

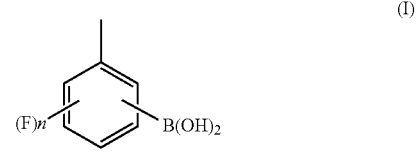  (I)

wherein F('s) is (are) present independently; n is 1, 2, 3, or 4; and when n is 1, the attachment positions of F and B(OH)₂ may be at any one of ortho, meta, and para,
the percentage of substituted PBA group-containing amino acid residues with respect to the total number of cationic amino acid residues in the polymer unit α is between 10-80%, and the percentage of substituted PBA binding site-containing amino acid residues with respect to the total number of cationic amino acid residues in the polymer unit β is between 5-80%.

2. The pharmaceutical composition according to claim 1, wherein the PBA binding site contains a gluconic acid derivative.

3. The pharmaceutical composition according to claim 1, wherein k is an integer of from 50 to 1,500.

4. The pharmaceutical composition according to claim 1, wherein at least one hydrogen of the phenyl ring of the substituted PBA group is substituted so as to have a pKa of approximately physiological pH.

5. The pharmaceutical composition according to claim 1, wherein the PBA groups of block copolymer α and the PBA binding sites of block copolymer β are selected such that there is a greater degree of cross linking of the phenylboronic acid group and the phenylboronic acid binding site when the micelle is disposed in an environment of pH 7 or higher than when the micelle is disposed in an environment of pH 6 or lower.

6. The pharmaceutical composition according to claim 5, wherein:
at least some of the PBA groups of block copolymer α form ester bonds with at least some of the PBA binding sites of block copolymer β when the micelle is disposed in an environment of pH 7 or higher, and
the ester bonds are prone to dissociate when the micelle is disposed in an environment of pH 4-6.

7. The pharmaceutical composition according to claim 1, wherein the nucleic acid is only pDNA.

8. The pharmaceutical composition according to claim 1, wherein the ratio between the contents of the block copolymer α and the block copolymer β in the micelle is from 2:3 to 3:2.

9. A pharmaceutical composition, comprising a micelle formed by block copolymers α and β, each having formula (1) or (2), wherein the block copolymer α and the block copolymer β are radially arranged in the micelle such that cationic polymer chain segments are directed inward and hydrophilic polymer chain segments are directed outward, and a nucleic acid encapsulated within the micelle,
wherein the formulas (1) and (2) are as follows:

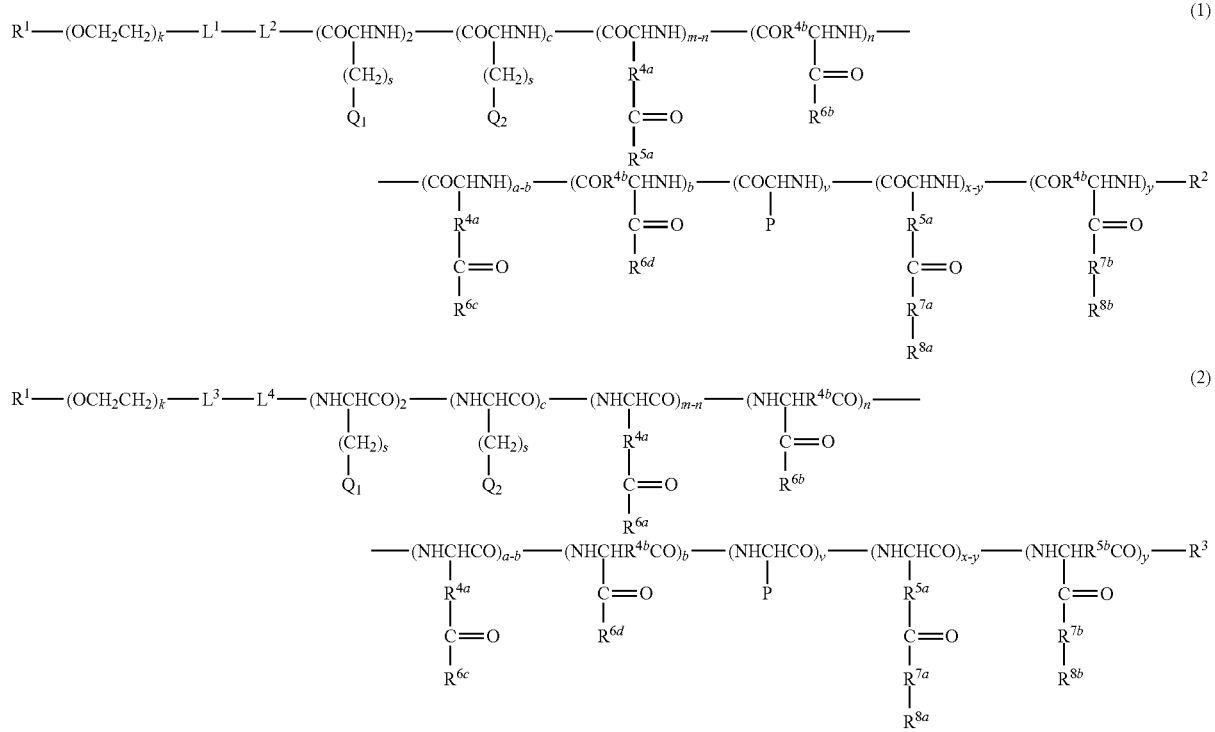

wherein:
R$^1$ is a hydrogen atom, an unsubstituted or substituted, linear or branched, alkyl group having 1 to 12 carbon atoms or a group containing a target binding site;

R$^2$ is a hydrogen atom, an unsubstituted or substituted, linear or branched, alkyl group having 1 to 12 carbon atoms, or an unsubstituted or substituted, linear or branched, alkylcarbonyl group having 1 to 24 carbon atoms;

R$^3$ is a hydroxyl group, an unsubstituted or substituted, linear or branched, alkyloxy group having 1 to 12 carbon atoms, an unsubstituted or substituted, linear or branched, alkenyloxy group having 2 to 12 carbon atoms, an unsubstituted or substituted, linear or branched, alkynyloxy group having 2 to 12 carbon atoms, or an unsubstituted or substituted, linear or branched, alkyl-substituted imino group having 1 to 12 carbon atoms;

R$^{4a}$, R$^{4b}$, R$^{5a}$, and R$^{5b}$ are each independently a methylene group or an ethylene group;

R$^{6a}$ and R$^{6b}$ are each independently a group selected from the following formulas (i) to (iv):

—NH—(CH$_2$)$_{p1}$—[NH—(CH$_2$)$_{q1}$—]$_{r1}$NH$_2$  (i);

—NH—(CH$_2$)$_{p2}$—N[—(CH$_2$)$_{q2}$—NH$_2$]$_2$  (ii);

—NH—(CH$_2$)$_{p3}$—N{[—(CH$_2$)$_{q3}$—NH$_2$][—(CH$_2$)$_{q4}$—NH—]$_{r2}$H}  (iii); and —NH—(CH$_2$)$_{p4}$—N{—(CH$_2$)$_{q5}$—N[—(CH$_2$)$_{q6}$—NH$_2$]$_2$}$_2$  (iv), wherein p1 to p4, q1 to q6, and r1 and r2 each are independently an integer of from 1 to 5;
$R^{6c}$ and $R^{6d}$ are each independently a group obtained by introducing a saturated or unsaturated, linear or branched, aliphatic hydrocarbon group having 6 to 27 carbon atoms, an aromatic hydrocarbon group having 6 to 27 carbon atoms, or a steryl group into an amino group of a group selected from the above formulas (i) to (iv);
$R^{7a}$ and $R^{7b}$ are each independently —O— or —NH—;
$R^{8a}$ and $R^{8b}$ are each independently a saturated or unsaturated, linear or branched, aliphatic hydrocarbon group having 6 to 27 carbon atoms, an aromatic hydrocarbon group having 6 to 27 carbon atoms, or a steryl group;
$Q_1$ is —NH$_2$, —NHC(=NH)NH$_2$, or a group having the following formula (II):

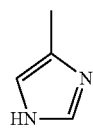

(II)

$Q_2$ is a group, in which a saturated or unsaturated, linear or branched, aliphatic hydrocarbon group having 6 to 27 carbon atoms, an aromatic hydrocarbon group having 6 to 27 carbon atoms, or a steryl group is introduced into an (the) amino group of —NH$_2$, —NHC(=NH)NH$_2$, or the group represented by said formula (II);
P is a side chain of leucine, isoleucine, phenylalanine, methionine, or tryptophan;
$L^1$ and $L^3$ are each independently —S—S— or a valence bond;
$L^2$ is —NH—, —O—, —O(CH$_2$)$_{p1}$—NH—, or -$L^{2a}$-(CH$_2$)$_{q1}$-$L^{2b}$-, where p1 and q1 are each independently an integer of from 1 to 5, $L^{2a}$ is OCO, OCONH, NHCO, NHCOO, NHCONH, CONH, or COO, and $L^{2b}$ is NH or O;
$L^4$ is —OCO—(CH$_2$)$_{p2}$—CO—, —NHCO—(CH$_2$)$_{p3}$—CO—, or -$L^{4a}$-(CH$_2$)$_{q2}$—CO—, where p2, p3, and q2 are each independently an integer of from 1 to 5, and $L^{4a}$ is OCONH, —CH$_2$NHCO—, NHCOO, NHCONH, CONH, or COO;
k is an integer of from 30 to 20,000;
s is an integer of from 1 to 6;
m is an integer of from 0 to 300;
n is an integer of from 0 to m;
a is an integer of from 0 to 300;
b is an integer of from 0 to a;
v is an integer of from 0 to 300;
c is an integer of from 0 to 300;
x is an integer of from 0 to 300;
y is an integer of from 0 to x;
z is an integer of from 0 to 300;
with the proviso that,
when m is 0, z is an integer of 2 or more;
when z is 0, m is an integer of 1 or more; and
when the sum of a total number of primary amino groups and secondary amino groups contained in (COCHNH)$_Z$ or (NHCHCO)$_Z$ and a total number of primary amino groups and secondary amino groups contained in (m-n) of $R^{6a}$ and n of $R^{6b}$, is defined as w, j hydrogen atom(s) of the amino group(s) is (are) each substituted with an organic group having a substituted phenylboronic acid (PBA) group in block copolymer α, and h hydrogen atom(s) of the amino group(s) is (are) each substituted with an organic group having a PBA binding site in block copolymer β, where j and h are each independently 1 or more but less than w;
PBA groups of block copolymer α are cross-linked to PBA binding sites of block copolymer β;
the PBA binding sites each contain a polyol having a cis-diol structure;
in the block copolymer α and the block copolymer β, the polyamino chain segment has a block structure or has a random structure, in which the binding order of the amino acid residues in the polyamino acid chain segment is arbitrary;
the nucleic acid is selected from the group consisting of pDNA or mRNA; and
the substituted PBA group has the following formula (I):

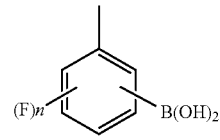

(I)

wherein F('s) is (are) present independently; n is 1, 2, 3, or 4; and when n is 1, the attachment positions of F and B(OH)$_2$ may be at any one of ortho, meta, and para, and
  the percentage of substituted PBA group-containing amino acid residues with respect to the total number of cationic amino acid residues in the polymer unit α is between 10-80%, and
  the percentage of substituted PBA binding site-containing amino acid residues with respect to the total number of cationic amino acid residues in the polymer unit β is between 5-80%.
10. The pharmaceutical composition according to claim 9, wherein the PBA binding site contains a gluconic acid derivative.
11. The pharmaceutical composition according to claim 9, wherein at least one hydrogen of the phenyl ring of the substituted PBA group is substituted so as to have a pKa of approximately physiological pH.
12. The pharmaceutical composition according to claim 9, wherein the PBA groups of block copolymer α and the PBA binding sites of block copolymer β are selected such that there is a greater degree of cross linking of the phenylboronic acid group and the phenylboronic acid binding site when the micelle is disposed in an environment of pH 7 or higher than when the micelle is disposed in an environment of pH 6 or lower.
13. The pharmaceutical composition according to claim 12, wherein:
  at least some of the PBA groups of block copolymer α form ester bonds with at least some of the PBA binding sites of block copolymer β when the micelle is disposed in an environment of pH 7 or higher, and the ester bonds are prone to dissociate when the micelle is disposed in an environment of pH 4-6.

14. The pharmaceutical composition according to claim 9, wherein the nucleic acid is only pDNA.

15. The pharmaceutical composition according to claim 9, wherein the ratio between the contents of the block copolymer α and the block copolymer β in the micelle is from 2:3 to 3:2.

* * * * *

UNITED STATES PATENT AND TRADEMARK OFFICE
CERTIFICATE OF CORRECTION

PATENT NO. : 10,993,960 B1
APPLICATION NO. : 15/309310
DATED : May 4, 2021
INVENTOR(S) : Kazunori Kataoka et al.

Page 1 of 1

It is certified that error appears in the above-identified patent and that said Letters Patent is hereby corrected as shown below:

In the Claims

In Claim 1, at Column 47, Line 48, the portion of Formula (1) reading -(COCHNH)$_2$- should read -(COCHNH)$_z$-.

In Claim 1, at Column 48, Line 43, the portion of Formula (2) reading -(COCHNH)$_2$- should read -(COCHNH)$_z$-.

In Claim 1, at Column 49, Line 21, replace "R$^b$" with "R$^{6b}$".

In Claim 9, at Column 52, Line 11, the portion of Formula (1) reading -(COCHNH)$_2$- should read -(COCHNH)$_z$-.

In Claim 9, at Column 52, Line 14, replace "R$^{5a}$" with "R$^{6a}$" in Formula (1).

In Claim 9, at Column 52, Line 15, the portion of Formula (1) reading -(COR$^{4b}$CHNH)$_y$- should read -(COR$^{5b}$CHNH)$_y$-.

In Claim 9, at Column 52, Line 19, the portion of Formula (2) reading -(COCHNH)$_2$- should read -(COCHNH)$_z$-.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*